US008328742B2

(12) United States Patent
Bledsoe

(10) Patent No.: US 8,328,742 B2
(45) Date of Patent: Dec. 11, 2012

(54) ADJUSTABLE ORTHOPEDIC BACK BRACE

(75) Inventor: Gary R. Bledsoe, Mansfield, TX (US)

(73) Assignee: Medical Technology Inc., Grand Prairie, TX (US)

(*) Notice: Subject to any disclaimer, the term of this patent is extended or adjusted under 35 U.S.C. 154(b) by 148 days.

(21) Appl. No.: 12/890,059

(22) Filed: Sep. 24, 2010

(65) Prior Publication Data
US 2011/0077567 A1 Mar. 31, 2011

Related U.S. Application Data

(60) Provisional application No. 61/245,922, filed on Sep. 25, 2009.

(51) Int. Cl.
*A61F 5/00* (2006.01)
*A61F 5/37* (2006.01)
(52) U.S. Cl. .......................................... 602/19; 128/846
(58) Field of Classification Search .................. 128/846,
128/869, 870, 873, 874, 875, 876; 602/20,
602/19, 5, 1, 32, 38, 35–36; 2/311, 312,
2/313–318, 322, 467, 44, 92
See application file for complete search history.

(56) References Cited

U.S. PATENT DOCUMENTS

| 1,184,581 | A | 5/1916 | Sigurini |
| 1,577,666 | A | 5/1926 | Walter |
| 1,667,989 | A | 5/1928 | Rocke |
| 1,727,668 | A | 9/1929 | Parkison |
| 2,036,484 | A | 4/1936 | LeMay |
| 2,100,964 | A | 11/1937 | Kendrick |
| 2,104,699 | A | 1/1938 | O'Dell |
| 2,117,309 | A | 5/1938 | Fritsch |
| 2,219,475 | A | 10/1940 | Flaherty |
| 2,285,612 | A | 6/1942 | Rehthaler |
| 2,449,641 | A | 9/1948 | Cidissen |
| 2,498,290 | A | 2/1950 | Morrison |

(Continued)

FOREIGN PATENT DOCUMENTS

DE 3613235 A1 11/1987

(Continued)

OTHER PUBLICATIONS

International Search Report and Written Opinion for International Application No. PCT/US2010/050185 dated Dec. 29, 2010.

(Continued)

*Primary Examiner* — Loan Thanh
*Assistant Examiner* — Tarla Patel
(74) *Attorney, Agent, or Firm* — K&L Gates LLP

(57) ABSTRACT

An adjustable orthopedic back brace includes: a first side panel having a distal end and a proximal end; a second side panel having a distal end and a proximal end; a rotating gear in geared communication with a first rack gear, the first rack gear connected to the proximal end of the first side panel, the rotating gear in geared communication with a second rack gear, the second rack gear connected to the proximal end of the second side panel; a mechanical advantage member rotatable with and providing mechanical advantage for the rotating gear; and an actuator connected operably to the mechanical advantage member for turning the member and the rotating gear to cause a translational movement of (i) the first rack gear and the first side panel and (ii) the second rack gear and the second side panel.

26 Claims, 17 Drawing Sheets

U.S. PATENT DOCUMENTS

| | | |
|---|---|---|
| 2,554,337 A | 5/1951 | Lampert |
| 2,733,712 A | 2/1956 | Wuesthoff |
| 2,749,550 A | 6/1956 | Pease |
| 3,052,236 A | 9/1962 | Schrieber |
| 3,096,760 A | 7/1963 | Nelkin |
| 3,097,640 A | 7/1963 | Morgan |
| 3,307,535 A | 3/1967 | Locke |
| 3,434,469 A | 3/1969 | Swift |
| 3,441,027 A | 4/1969 | Lehman |
| 3,452,748 A | 7/1969 | Caprio |
| 3,554,190 A | 1/1971 | Kaplan |
| 3,561,436 A | 2/1971 | Gaylord, Jr. |
| 3,568,670 A | 3/1971 | Gaylord, Jr. |
| 3,570,480 A | 3/1971 | Stubbs |
| 3,578,773 A | 5/1971 | Schultz |
| 3,598,114 A | 8/1971 | Lewis |
| 3,603,316 A | 9/1971 | Lehman |
| 3,623,488 A | 11/1971 | Nakayama |
| 3,717,143 A | 2/1973 | Johnson |
| 3,920,008 A | 11/1975 | Lehman |
| 3,926,183 A | 12/1975 | Spiro |
| 3,927,665 A | 12/1975 | Wax |
| 4,099,524 A | 7/1978 | Cueman et al. |
| 4,135,503 A | 1/1979 | Romano |
| 4,175,553 A | 11/1979 | Rosenberg |
| 4,178,922 A | 12/1979 | Curlee |
| 4,178,923 A | 12/1979 | Curlee |
| 4,245,628 A | 1/1981 | Eichler |
| 4,390,014 A | 6/1983 | Forman |
| 4,459,979 A | 7/1984 | Lewis, Jr. |
| 4,475,543 A | 10/1984 | Brooks et al. |
| 4,508,110 A | 4/1985 | Modglin |
| 4,527,289 A | 7/1985 | Shea |
| 4,545,370 A | 10/1985 | Welsh |
| 4,572,167 A | 2/1986 | Brunswick |
| 4,622,957 A | 11/1986 | Curlee |
| 4,627,109 A | 12/1986 | Carabelli et al. |
| 4,681,113 A | 7/1987 | Coplans |
| 4,721,102 A | 1/1988 | Pethybridge |
| 4,745,911 A | 5/1988 | Bender |
| 4,756,306 A | 7/1988 | Curlee |
| 4,794,916 A | 1/1989 | Porterfield et al. |
| 4,833,730 A | 5/1989 | Nelson |
| 4,836,194 A | 6/1989 | Sebastian et al. |
| 4,964,401 A | 10/1990 | Taigen |
| 4,991,234 A | 2/1991 | Greenberg |
| 4,991,573 A | 2/1991 | Miller |
| 4,992,234 A | 2/1991 | Ohashi et al. |
| 4,993,409 A | 2/1991 | Grim |
| 5,007,412 A | 4/1991 | DeWall |
| 5,036,864 A | 8/1991 | Yewer, Jr. |
| 5,040,524 A | 8/1991 | Votel et al. |
| 5,046,488 A | 9/1991 | Schiek, Sr. |
| 5,062,414 A | 11/1991 | Grim |
| 5,070,866 A | 12/1991 | Alexander et al. |
| 5,072,725 A | 12/1991 | Miller |
| 5,086,758 A | 2/1992 | Schiek, Sr. et al. |
| 5,086,759 A | 2/1992 | Buddingh |
| 5,105,806 A | 4/1992 | Woodhouse et al. |
| 5,111,806 A | 5/1992 | Travis |
| 5,111,807 A | 5/1992 | Spahn et al. |
| 5,122,111 A | 6/1992 | Sebastian et al. |
| 5,147,261 A | 9/1992 | Smith et al. |
| 5,148,549 A | 9/1992 | Sydor |
| 5,176,131 A | 1/1993 | Votel et al. |
| 5,178,163 A | 1/1993 | Yewer, Jr. |
| 5,179,942 A | 1/1993 | Drulias et al. |
| 5,188,585 A | 2/1993 | Peters |
| 5,188,586 A | 2/1993 | Castel et al. |
| 5,195,948 A | 3/1993 | Hill et al. |
| 5,205,814 A | 4/1993 | Lundrigan et al. |
| 5,205,815 A | 4/1993 | Saunders |
| 5,207,635 A | 5/1993 | Richards |
| 5,207,636 A | 5/1993 | Striano |
| 5,226,874 A | 7/1993 | Heinz et al. |
| 5,232,424 A | 8/1993 | Pearson |
| 5,241,704 A | 9/1993 | Sydor |
| 5,257,419 A | 11/1993 | Alexander |
| 5,259,831 A | 11/1993 | LeBron |
| 5,267,947 A | 12/1993 | James |
| 5,302,171 A | 4/1994 | Pearson |
| 5,310,401 A | 5/1994 | Striano |
| 5,316,022 A | 5/1994 | Schiek, Sr. |
| 5,318,505 A | 6/1994 | Sou |
| 5,318,507 A | 6/1994 | Greengarg |
| 5,334,134 A | 8/1994 | Saunders |
| 5,346,461 A | 9/1994 | Heinz et al. |
| 5,351,340 A | 10/1994 | Aldridge |
| 5,363,863 A | 11/1994 | Lelli et al. |
| 5,387,183 A | 2/1995 | Jones |
| 5,388,273 A | 2/1995 | Sydor et al. |
| 5,388,274 A | 2/1995 | Glover et al. |
| 5,396,906 A | 3/1995 | Harrold |
| 5,399,150 A | 3/1995 | Saunders |
| 5,399,151 A | 3/1995 | Smith |
| 5,421,809 A | 6/1995 | Rise |
| 5,426,791 A | 6/1995 | Sydor et al. |
| 5,429,587 A | 7/1995 | Gates |
| 5,432,951 A | 7/1995 | Yewer, Jr. |
| 5,433,697 A | 7/1995 | Cox |
| 5,437,615 A | 8/1995 | Pekar et al. |
| 5,437,617 A | 8/1995 | Heinz et al. |
| 5,445,601 A | 8/1995 | Harlow |
| 5,447,498 A | 9/1995 | Watson |
| 5,450,627 A | 9/1995 | Grilliot |
| 5,450,858 A | 9/1995 | Zablotsky et al. |
| 5,470,000 A | 11/1995 | Munoz |
| 5,484,395 A | 1/1996 | DeRoche |
| 5,489,260 A | 2/1996 | Striano |
| 5,499,965 A | 3/1996 | Sanchez |
| 5,500,959 A | 3/1996 | Yewer, Jr. |
| 5,503,620 A | 4/1996 | Danzger |
| 5,533,961 A | 7/1996 | Iwata |
| 5,536,246 A | 7/1996 | Saunders |
| 5,547,462 A | 8/1996 | Lanigan et al. |
| 5,548,843 A | 8/1996 | Chase et al. |
| 5,551,085 A | 9/1996 | Leighton |
| 5,560,046 A | 10/1996 | Iwamasa et al. |
| 5,581,810 A | 12/1996 | Yewer, Jr. |
| 5,586,969 A | 12/1996 | Yewer, Jr. |
| 5,591,122 A | 1/1997 | Yewer, Jr. |
| 5,598,583 A | 2/1997 | Victor |
| 5,599,287 A | 2/1997 | Beczak, Sr. et al. |
| 5,611,084 A | 3/1997 | Garry et al. |
| 5,628,721 A | 5/1997 | Arnold et al. |
| 5,634,891 A | 6/1997 | Beczak, Sr. et al. |
| 5,651,763 A | 7/1997 | Gates |
| 5,656,020 A | 8/1997 | Greengarg |
| 5,656,021 A | 8/1997 | Greengarg |
| 5,690,122 A | 11/1997 | Weber-Unger |
| 5,690,609 A | 11/1997 | Heinze, III |
| 5,693,006 A | 12/1997 | Slautterback |
| 5,722,940 A | 3/1998 | Gaylord, Jr. et al. |
| 5,728,055 A | 3/1998 | Sebastian |
| 5,762,619 A | 6/1998 | Simon |
| 5,765,224 A | 6/1998 | Johnson |
| 5,776,087 A | 7/1998 | Nelson et al. |
| 5,782,782 A | 7/1998 | Miller |
| 5,785,671 A | 7/1998 | Striano |
| 5,785,672 A | 7/1998 | Mattison et al. |
| RE35,940 E | 10/1998 | Heinz et al. |
| 5,820,575 A | 10/1998 | Cabrera et al. |
| 5,833,638 A | 11/1998 | Nelson |
| 5,853,378 A | 12/1998 | Modglin |
| 5,865,774 A | 2/1999 | Brenman et al. |
| 5,934,599 A | 8/1999 | Hammerslag |
| 5,967,998 A | 10/1999 | Modglin |
| 5,984,885 A | 11/1999 | Gaylord, Jr. et al. |
| 5,984,886 A | 11/1999 | Miller |
| 6,053,883 A | 4/2000 | Schiek, Sr. |
| 6,068,606 A | 5/2000 | Castel et al. |
| 6,080,121 A | 6/2000 | Madow et al. |
| 6,099,490 A | 8/2000 | Turtzo |
| 6,137,675 A | 10/2000 | Perkins |
| 6,146,345 A | 11/2000 | Mignard |
| 6,156,001 A | 12/2000 | Frangi et al. |
| 6,165,147 A | 12/2000 | Morrow |

| | | |
|---|---|---|
| 6,190,343 B1 | 2/2001 | Heinz et al. |
| 6,213,968 B1 | 4/2001 | Heinz et al. |
| 6,289,558 B1 | 9/2001 | Hammerslag |
| 6,319,217 B1 | 11/2001 | Darcey |
| 6,322,529 B1 | 11/2001 | Chung |
| 6,336,908 B1 | 1/2002 | Slautterback |
| 6,342,044 B1 | 1/2002 | Frangi et al. |
| 6,419,652 B1 | 7/2002 | Slautterback |
| 6,478,759 B1 | 11/2002 | Modglin et al. |
| 6,500,137 B1 | 12/2002 | Molino et al. |
| 6,503,215 B1 | 1/2003 | Reinhardt et al. |
| 6,517,502 B2 | 2/2003 | Heyman et al. |
| 6,524,264 B1 | 2/2003 | Hutchinson |
| 6,533,740 B2 | 3/2003 | Reinecke et al. |
| 6,602,214 B2 | 8/2003 | Heinz et al. |
| 6,609,642 B1 | 8/2003 | Heinz et al. |
| 6,610,022 B1 | 8/2003 | Ashbaugh et al. |
| 6,635,025 B1 | 10/2003 | Reinecke et al. |
| 6,666,838 B2 | 12/2003 | Modglin et al. |
| 6,689,082 B2 | 2/2004 | Reinecke et al. |
| 6,702,770 B2 | 3/2004 | Bremer et al. |
| 6,702,771 B1 | 3/2004 | Reinecke et al. |
| 6,746,413 B2 | 6/2004 | Reinecke et al. |
| 6,755,799 B2 | 6/2004 | Toda |
| 6,766,532 B1 | 7/2004 | Cabana |
| 6,776,767 B2 | 8/2004 | Reinecke et al. |
| 6,840,916 B2 | 1/2005 | Kozersky |
| 6,896,662 B2 | 5/2005 | Heffez |
| 6,921,375 B2 | 7/2005 | Kihara |
| 6,923,779 B1 | 8/2005 | Choiniere |
| 6,932,780 B2 | 8/2005 | Kozersky |
| 6,951,547 B1 | 10/2005 | Park et al. |
| 6,962,572 B1 | 11/2005 | Zahiri |
| 6,964,644 B1 | 11/2005 | Garth |
| 6,974,432 B2 | 12/2005 | Reinecke et al. |
| 6,997,892 B2 | 2/2006 | Reinecke |
| 7,001,350 B2 | 2/2006 | Grosso |
| 7,001,351 B2 | 2/2006 | Reinecke et al. |
| 7,025,737 B2 | 4/2006 | Modglin |
| 7,037,284 B2 | 5/2006 | Lee |
| 7,070,572 B2 | 7/2006 | Reinecke et al. |
| 7,074,201 B2 | 7/2006 | Reinecke et al. |
| 7,077,794 B1 | 7/2006 | Bray |
| 7,083,585 B2 | 8/2006 | Latham |
| 7,101,348 B2 | 9/2006 | Garth et al. |
| 7,118,543 B2 | 10/2006 | Telles et al. |
| 7,160,262 B2 | 1/2007 | Wicks |
| 7,186,229 B2 | 3/2007 | Schwenn et al. |
| 7,201,727 B2 | 4/2007 | Schwenn et al. |
| 7,276,038 B2 | 10/2007 | Reinecke et al. |
| 7,306,571 B2 | 12/2007 | Schwenn et al. |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,322,952 B2 | 1/2008 | Chase et al. |
| 7,329,231 B2 | 2/2008 | Frank |
| 7,364,558 B2 | 4/2008 | Weaver, II et al. |
| 7,371,222 B2 | 5/2008 | Heinz et al. |
| 7,445,608 B2 * | 11/2008 | Dunfee et al. ............... 602/19 |
| 7,449,005 B2 | 11/2008 | Pickering et al. |
| 2001/0008955 A1 | 7/2001 | Garth |
| 2001/0020144 A1 | 9/2001 | Heinz et al. |
| 2002/0068890 A1 * | 6/2002 | Schwenn et al. ............... 602/19 |
| 2002/0123705 A1 | 9/2002 | Reinecke et al. |
| 2002/0193720 A1 | 12/2002 | Reinecke et al. |
| 2003/0050585 A1 | 3/2003 | Modglin |
| 2003/0097085 A1 | 5/2003 | Reinecke et al. |
| 2004/0167449 A1 | 8/2004 | Heffez et al. |
| 2004/0220502 A1 | 11/2004 | Arden |
| 2005/0015034 A1 | 1/2005 | Sansone et al. |
| 2005/0043660 A1 | 2/2005 | Stark et al. |
| 2005/0267390 A1 | 12/2005 | Garth et al. |
| 2006/0129077 A1 | 6/2006 | Parizot |
| 2006/0282032 A1 | 12/2006 | Smith et al. |
| 2007/0073204 A1 | 3/2007 | Suarez et al. |
| 2007/0156073 A1 | 7/2007 | Smith |
| 2007/0197943 A1 | 8/2007 | Hakonson et al. |
| 2008/0004557 A1 | 1/2008 | Wolanske |
| 2008/0045873 A1 | 2/2008 | Zours |
| 2008/0171955 A1 | 7/2008 | Jaccard |

FOREIGN PATENT DOCUMENTS

| | | |
|---|---|---|
| EP | 410904 A1 | 1/1991 |
| EP | 459082 A1 | 12/1991 |
| FR | 2569344 A1 | 2/1986 |
| GB | 2120100 A | 11/1983 |
| JP | 6078943 A | 3/1994 |
| WO | WO9005502 A1 | 5/1990 |
| WO | WO9318724 A1 | 9/1993 |
| WO | WO9412125 A1 | 6/1994 |
| WO | 9965428 | 12/1999 |
| WO | 2008037584 | 4/2008 |

OTHER PUBLICATIONS

U.S. Appl. No. 13/116,687, filed May 26, 2011, Hendricks.

International Preliminary Report on Patentability for International Application No. PCT/US2010/050185 mailed Sep. 30, 2011.

* cited by examiner

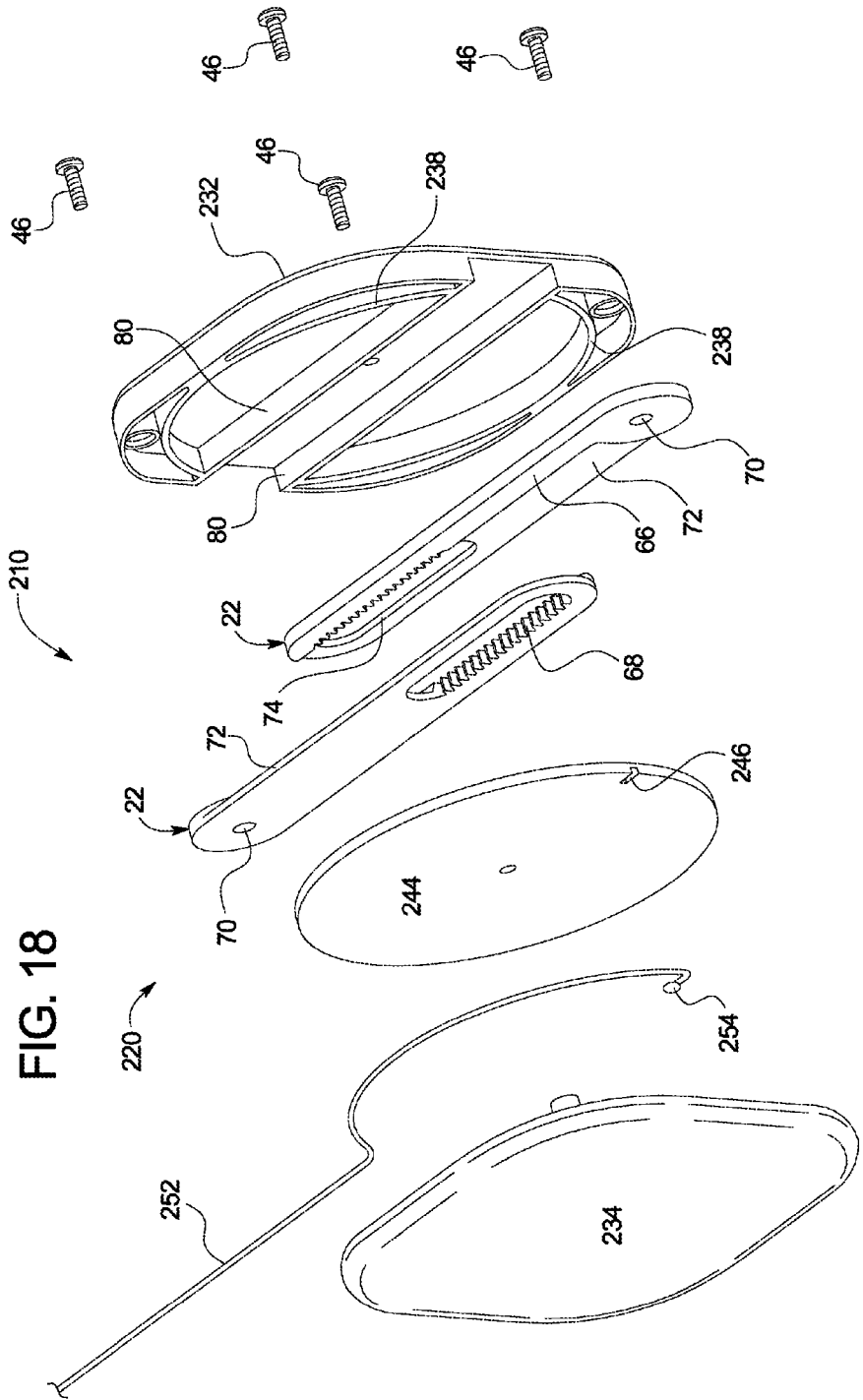

ADJUSTABLE ORTHOPEDIC BACK BRACE

PRIORITY CLAIM

This application claims priority to and the benefit of U.S. provisional patent Application No. 61/245,922, entitled "Adjustable Orthopedic Back Brace", filed Sep. 25, 2009, the entire contents of which are incorporated herein by reference and relied upon.

BACKGROUND

The present disclosure relates to orthopedic back braces: Adjustable orthopedic back braces are known in the art. Certain of such braces employ motors for adjustment. Other braces have a set of pulleys mounted on each of two brace segments with a cable running through the pulleys in alteration for adjustment.

The drawbacks associated with requiring a motor for adjustment should be readily apparent. The motor is relatively costly, requires power, adds weight and can wear out. An adjustable orthopedic back brace that does not require a motor is therefore desirable.

Braces having a pair of back brace segments tensioned via pulleys on each of the braces also have drawbacks. First, the dual brace segments requiring a cable to run back and forth between the segments are complicated and cumbersome. Second, the dual brace segments reside on each side of the wearer's spine, such that the spine itself is not directly engaged by the segments or resulting brace without a separate pad. In many instances, the wearer's lower spine is the source of pain and/or the reason for wearing the brace. Further, placing the cabling mechanisms on either side of the spine causes a centered back position to be maintained only if both pull handles are adjusted simultaneously.

An improved manually adjustable back brace is therefore needed.

SUMMARY

The present disclosure sets forth multiple primary embodiments for a manually adjustable orthopedic back brace, namely, a gear-on-gear embodiment or version, a multiple gear-on-pulley embodiment or version and a single gear-on-pulley (or gear-on-gear) embodiment. Each embodiment includes left and right flexible side panels that attach moveably at their proximal, backside or posterior ends to an adjustment assembly located at the posterior center or spine of the patient. In each embodiment, the distal, frontal or anterior ends of the side panels connect together at the patient's front or stomach. The patient pulls a pull handle in each embodiment to tighten the brace or loosens the pull handle to allow the brace to be expanded or loosened. Each embodiment includes or is operable with accessories, such as a posterior back plate that fits between the patient's back and the adjustment assembly. An inflatable pad can additionally be located between the plate and the patient's back. An anterior plate and/or inflatable pad can further be provided for the front of the patient.

The multiple gear-on-gear version or first primary embodiment of the adjustment assembly includes two injection molded gear sets, each set having a smaller inner gear, e.g., sixteen tooth by 0.125 inch (3.2 mm) thick, molded concentrically with a larger outer gear, e.g., ninety-six tooth by 0.125 inch (3.2 mm) thick. The outer gears of the gear sets are separated by an, e.g., injection molded, adjuster strap, which has a handle portion for pulling the strap and a rack gear portion for operating with the larger gears of each gear set. The handle portion can be thicker than the rack gear portion. A transition portion of the strap between the handle portion and the rack gear portion has a slight cutout or indent that allows the strap to be releasably held at its most retracted or withdrawn position.

The gear sets and a portion of the adjuster strap reside inside a housing, which can be formed from two injection molded halves. The gear sets and housing halves can be made of a tough material, such as a glass-filled, self lubricating plastic. The front housing half (facing away from the wearer when brace is worn) is fitted with two polished, e.g., 0.125 inch (3.2 mm) diameter, stainless steel pivot pins upon each of which one of the two gear sets rotates. The housing halves include or define designated channel walls within which the adjuster strap (both handle and rack gear portions thereof) slide and within which the gear sets rotate.

The inner, smaller gears each communicate with a pair of retraction rack gears. The retraction rack gears can be about 0.115 inch (2.9 mm) thick at its widest point and be made from the same plastic as the housing and the gear sets. The retraction rack gears of each pair have a stepped thickness so that when mated, the linear gears of each rack lie in the same plane. Each rack has a gear slot. The linear gears are each formed on one edge of each slot. When mated, the geared edges oppose each other by a distance that is substantially equal to the diameter of the mating smaller, inner gear.

The side panels each attach to the distal or anterior ends of the rack gears. To this end, the rear or proximal end of each side panel includes a tough but flexible sew-on tab reinforcement, which defines attachment holes for mating with holes formed in the distal ends of the rack gears. Pulling the handle of the adjuster strap out from the gear housing causes the retraction rack gears to retract inwards towards the gear housing centerline (roughly coextensive with wearer's spine), which in turn pull the side panels towards the gear housing. Like the handle and associated rack gear of the adjuster strap, the outer and inner retraction rack gears are each guided within channels formed in the housing.

The side panels are each made of a flexible mesh trampoline material in one embodiment. One of the side panels has a channel formed by two stiffer polyester films laid back-to-back and sealed at their edges. The two polyester film strips are, in one embodiment, exactly the same size and shape as a third, outer, pile fabric strip. The films and strip are stacked on top of one another in the following order: the polyester film, the second polyester film and the pile strip. The stack is then sewn on three sides of its perimeter to the trampoline mesh material of the side panel, leaving an oval opening at its proximal end, such that the pile material faces outwardly to provide a location at which to attach a mating hook material. The resulting channel encases the rack gear portion of the adjuster strap between the polyester strips, so that the distal rack gear portion of the strap is contained within the channel and forced to wrap around the waist of the wearer, preventing the rack gear portion from sticking out into the air.

The other mesh trampoline panel has its own pile strip sewn down its middle to accept and hold a hook material placed on the underside of the handle of the adjuster strap at a position in which the wearer has pulled (or loosened) the strap. The overall brace is then tensioned to a desired level.

A right-hand panel (viewed from the back of the wearer) extends from the right of the wearer's spine, around to the front of the patient's waist with its anterior or distal end extending slightly past the midline of the wearer's front. The left-hand panel extends from the left of the wearer's spine, around to the front of the patient's waist with its anterior or distal end extending slightly past the midline of the wearer's front, such that the anterior or distal ends of the panels can be attached to each other. It is contemplated to provide the brace in different sizes, e.g., small, medium and large. The anterior end of one of the side panels has hook material sewn to the underside of the mesh trampoline material to engage a pile surface sewn to the outside of the anterior end of the other side panel.

When the adjustment handle is in its most retracted (pushed-in) position, the rack gear portion of the adjuster strap extends its furthest into the channel formed by the polyester strips beneath the pile strip of the, e.g., right-hand panel (viewed from the back of the wearer). When the retraction rack gears are in their most extended position, the waist circumference of the side panels is at its maximum. After the user lifts the pull handle from the pile strip on the left-hand panel (viewed from the back of the wearer) and pulls the pull handle to the left (viewed from the back of the wearer), the rack gears in turn move inwardly and pull the two side panels closer to the gear housing to adjust tension on the brace to a desired level. The wearer then presses the pull handle back onto the pile strip of the left-hand panel (viewed from the back of the wearer) to hold the brace in an adjusted and tensioned position.

In the second version or multiple gear-on-pulley primary embodiment, the larger gears of the gear-on-gear version are replaced with pulleys. The rack gear portion of the adjuster is replaced with a cord that attaches to the pulleys. The versions are otherwise very similar. In particular, the outer ninety-six tooth gears of the gear-on-gear version are replaced with two equivalent diameter pulleys. A cord is affixed to each of the pulleys and is wrapped around the pulleys making enough turns to provide sufficient cord length for the total travel of the rack gears. The cord then runs from the larger pulleys to a balancer pulley located on the adjuster handle, which has hook material located on its opposing surface as before, to lock the brace in a desirably tensioned position.

The multiple gear-on-pulley version includes the mating inner and outer retraction rack gears discussed above for the gear-on-gear version, which again operate in geared relation with small central gears, here located at the center of each large pulley. The retraction rack gears adjust the panels in the same manner as described above for the gear-on-gear version. Pulling the adjusting handle outwardly pulls the cable or cord out of the gear housing and causes the two large pulleys to turn and thereby retract (move inwardly) the four rack gears to tighten the right and left side panels. The side panels are the same as described above for the gear-on-gear version, except that the right-hand panel (as described in the example above) does not need the channel to receive the rack gear portion of the adjuster, which does not exist with the gear-on-pulley version of the brace.

In an alternative embodiment of the gear-on-pulley adjustable back brace, only a single pulley is provided. A cord is affixed to the pulleys and is wrapped around the pulley, e.g., one-half way around the pulley, to obtain sufficient turning friction with the pulley. The cord then runs from the larger pulley directly to the adjuster handle (balancer pulley not needed), which has hook material located on its opposing surface as before, to lock the brace in a desirably tensioned position.

The single gear-on-pulley version includes mating inner and outer retraction rack gears (here only one set) like the ones discussed above for the gear-on-gear version and multiple gear-on-pulley version, which again operate in geared relation with a small central gear located at the center of the large pulley. The retraction rack gears adjust the panels in the same manner as described above for the gear-on-gear version and multiple gear-on-pulley version. Pulling the adjusting handle outwardly pulls the cable or cord out of the gear housing and causes the large pulley to turn and thereby retract (move inwardly) the two mating rack gears to tighten the right and left side panels. The side panels are the same as described above for the multiple gear-on-pulley version, except that the single pulley is centered vertically relative to the side panels. The rack gears of the single rack gear set mate with the single rotary gear located at the center of the single pulley, such that the outer attachment portions of the rack gears form a single, central point of attachment to a respective one of the side panels.

It is also contemplated to provide a single gear-on-sear adjustable back brace as discussed further below.

The gear-on-gear and gear-on-pulley versions of the brace are each operable with various accessories. For example, all versions can be used with an optional back plate, which may be attached to the gear-on-pulley or gear-on-gear housing via a suitable detachable apparatus, such as a snap- or slide-lock fit or hook and pile engagement. The optional back plate can have a shape contoured for the wearer's spine or simply be flat, which in either case provides additional support for the wearer's back. The back plate can be rotated or flipped relative to the adjustment housing to allow for left-handed or right-handed operation. Alternatively, the back plate is not rotable and the back brace is made in left-handed and right-handed versions. The back plate can be detachable and carry accessory pads or an air bladder to aid in the padding or conforming ability of the brace to the lumbar area of a patient's back. If a back plate is not provided, the pads or air bladder can alternatively be attached directly to the gear-on-pulley or gear-on-gear adjustment housing.

The air bladder can be operated with a hand air pump that the wearer couples to an inlet port of the bladder. The wearer squeezes the hand pump a number of times until the air bladder is filled to a pressure desired by the user. Either or both of the back plate and the air bladder can be used alternatively at the front side or anterior side of the user.

It is accordingly an advantage of the present disclosure to provide a back brace that places the housing or back panel of the brace in a centered position on the lumbar spine.

It is another advantage of the present disclosure to provide a back brace for which a centered back position can be maintained by pulling a single handle.

It is a further advantage of the present disclosure to provide a back brace for which air bladders and/or other molded back pads can be detachably fastened in a centered position without having to change position of the side panels.

It is yet another advantage of the present disclosure to provide a back brace that is comfortable for the wearer and promotes spinal alignment.

It is still a further advantage of the present disclosure to provide a back brace that allows for user coning or non-uniformity of the user's body diameter extending from the bottom of the brace at the base of the patient's back upwards along the patient's spine.

Additional features and advantages are described herein, and will be apparent from the following Detailed Description and the figures.

BRIEF DESCRIPTION OF THE FIGURES

FIG. 18 is an exploded perspective view of one embodiment of an adjustment assembly for a single gear-on-pulley version of the adjustable back brace of the present disclosure.

DETAILED DESCRIPTION

Common Side Panels and Other Features

Figure 1:
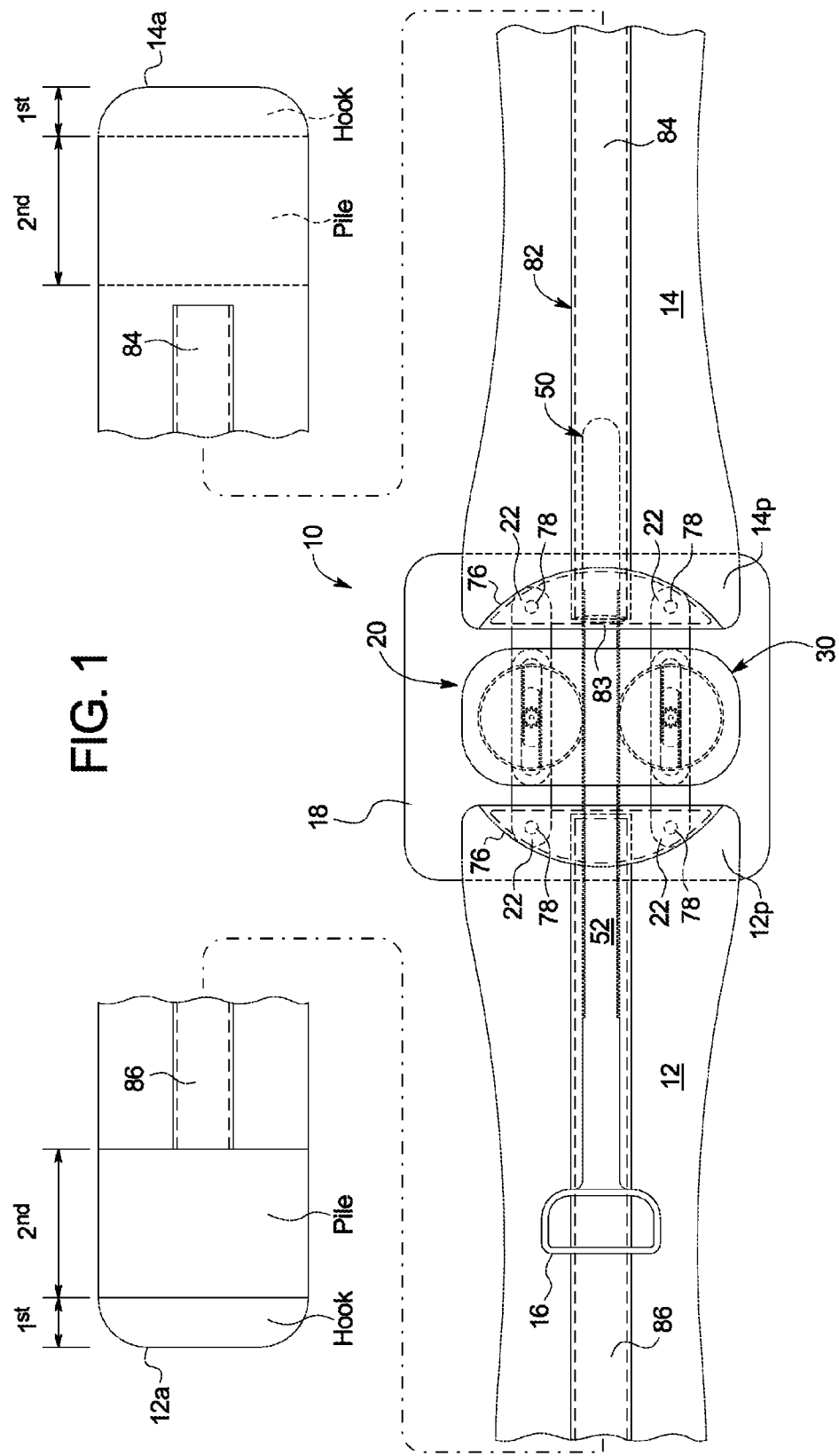
FIG. 1 is an elevation view of one embodiment of a gear-on-gear version of the adjustable back brace of the present disclosure.

Referring now to the drawings, the present disclosure sets forth multiple embodiments for a manually adjustable orthopedic back brace, namely, a gear-on-gear brace 10 (FIGS. 1 to 7), a multiple gear-on-pulley brace 110 (FIGS. 8 to 12) and a single gear-on-pulley brace 210 (FIGS. 15 to 18). As illustrated in FIG. 1, each of the embodiments 10, 110 and 210 includes left and right flexible side panels 12 and 14, which each attach at their backside or proximal ends 12p and 14p, respectively, to rack gears 22 of an adjustment assembly (20 or 120) located at the posterior center or spine of the patient. In each embodiment 10, 110 and 120, the frontal or distal ends 12a and 14a, respectively, of side panels 12 and 14 connect together at the patient's front or stomach. The patient pulls a pull handle 16 in each version to tighten the brace or loosens the pull handle to allow the brace to be expanded or loosened. Each embodiment includes accessories, such as a posterior back plate 18 that fits between the patient's back and the adjustment assembly. An inflatable pad 118 (FIGS. 13 and 14) can additionally be located between back plate 18 and the patient's hack. An anterior plate and/or inflatable pad can also be provided for application at the front of the patient.

Multiple Gear-on-Gear

Figure 2:
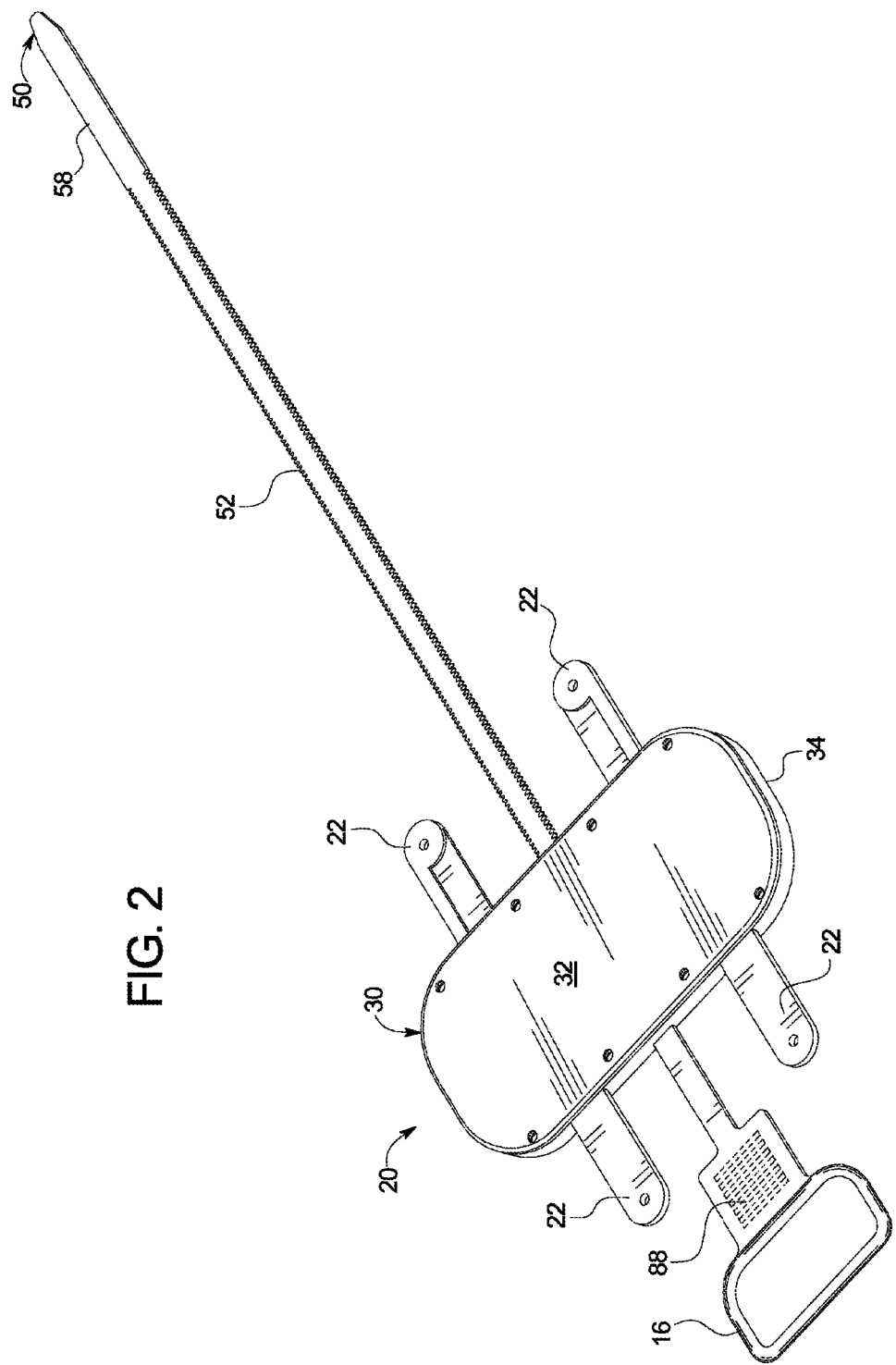
FIG. 2 is a perspective view of an assembled adjustment assembly for the gear-on-gear embodiment of FIG. 1.
Figure 3:
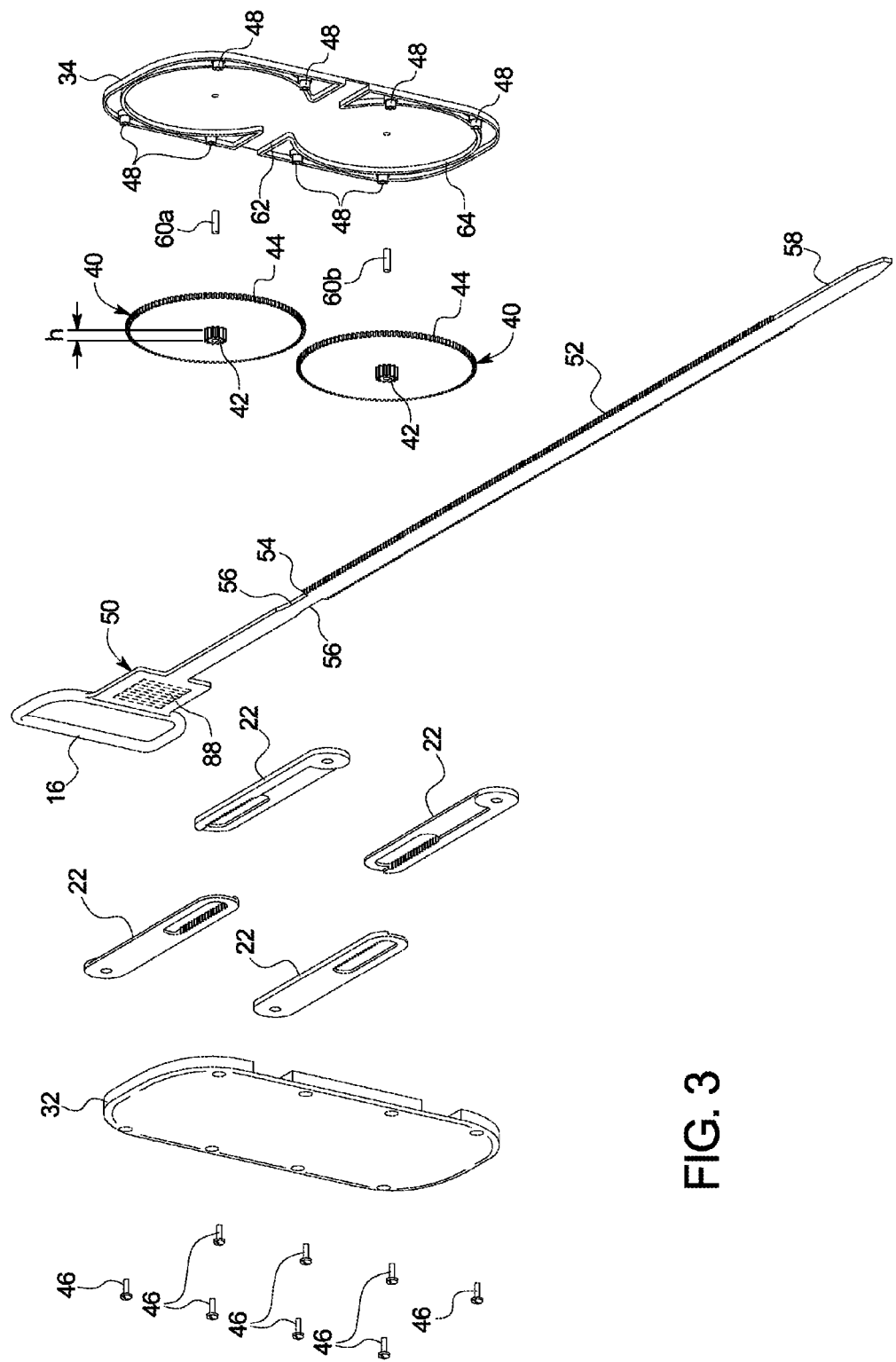
FIG. 3 is an exploded view of an adjustment assembly for the gear-on-gear embodiment of FIG. 1.

Referring to FIGS. 1 to 7, a gear-on-gear adjustment assembly 20 includes a housing 30 having a back plate 32 (shown as providing, through-holes for screws) and a front plate 34 (shown as providing, threaded inserts for screws). Either plate 32 and 34 can be made of plastic, such as acrylonitrile butadiene styrene ("ABS") or nylon. The material can be opaque, semi-opaque or clear. FIG. 3 in particular shows that in one embodiment, screws or fasteners 46 are inserted through the through-holes made in back plate 32 and threaded into threaded inserts 48 formed in front plate 34.

Back plate 32 (positioned closer to the wearer's back) and a front plate 34 (positioned further from the wearer's back and facing outwardly) each hold two injection molded gear sets 40. Each gear set 40 has a smaller inner gear 42, e.g., sixteen tooth by 0.125 inch (3.2 mm) thick, molded concentrically with a larger outer gear 44, e.g., ninety-six tooth by 0.125 inch (3.2 mm) thick. Gear sets 40 are made of tough material, such as a glass-filled, self lubricating plastic, liquid crystal plastic.

The outer gears 44 of gear sets 40 are separated for example by an injection molded, adjuster strap or actuator 50, which has handle portion 16 (mentioned above) and a rack gear portion 52. Adjuster strap 50 can be made of any of the materials discussed herein for housing 30 and gear sets 40. Handle portion 16 is in one embodiment thicker than rack gear portion 52, e.g., 0.188 inch (4.8 mm) thick. A transition portion 54 of the strap is located between the handle portion 16 and the rack gear portion 52. Transition portion 54 has a slight cutouts or indents 56 on both of its edges (shown best in FIGS. 4 and 5), which allow strap 50 to be held releasably at its most retracted or pushed-in, brace-expanded, position. A distal end 58 of actuator 50 is not geared and has a width that is at least as wide as the widest width of rack gear portion 52, such that actuator 50 cannot be pulled completely out from between gear sets 40. That is, the transitioning edge of distal end 58 will wedge between larger gears 44, preventing strap 50 from being pulled through the gears.

Figure 4:
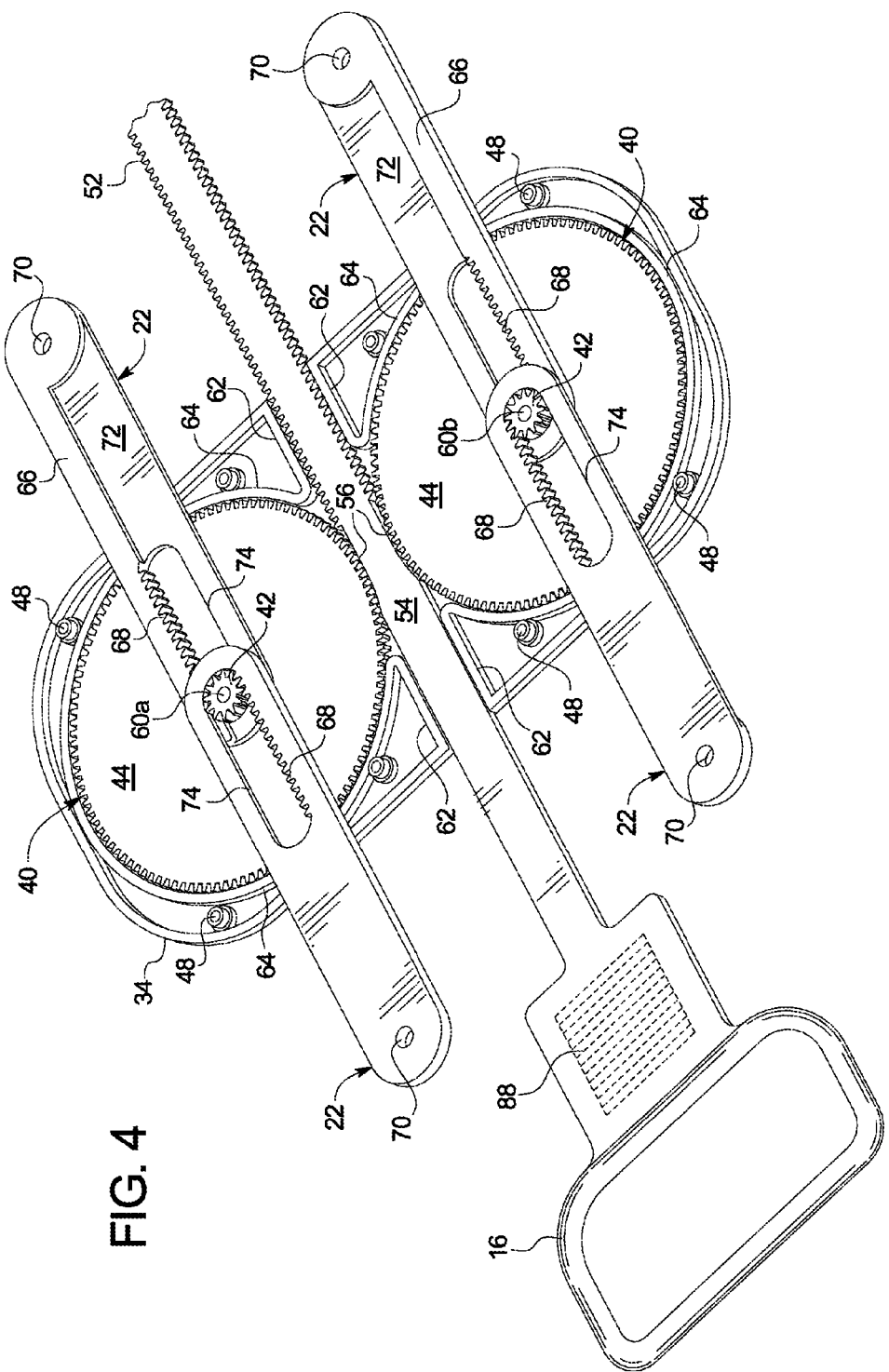
FIG. 4 is a perspective view of the adjustment assembly for the gear-on-gear embodiment of FIG. 1, having the back plate removed to view the smaller gears of the gear sets and the hook material of the handle, the smaller gears and hook material facing towards the wearer's back when worn.

Gear sets 40 and a portion of adjuster strap or actuator 50 reside inside housing 30. FIGS. 3 and 4 show that front plate 34 is fitted with two polished, e.g., 0.125 inch (3.2 mm) diameter, stainless steel pivot pins 60a and 60b upon which gear sets 40 rotate respectively. In another embodiment, all screws, threads and pins are made of a tough plastic, such that the brace can be worn through a metal detector without having to remove the brace. Front plate 34 includes or defines channel-forming walls 62 within which the adjuster strap or actuator 50 slides. Likewise, circular walls 64 formed on the inside surface of front plate 34 guide the placement of larger gears 44 as seen in FIGS. 3 and 4.

Figure 5:
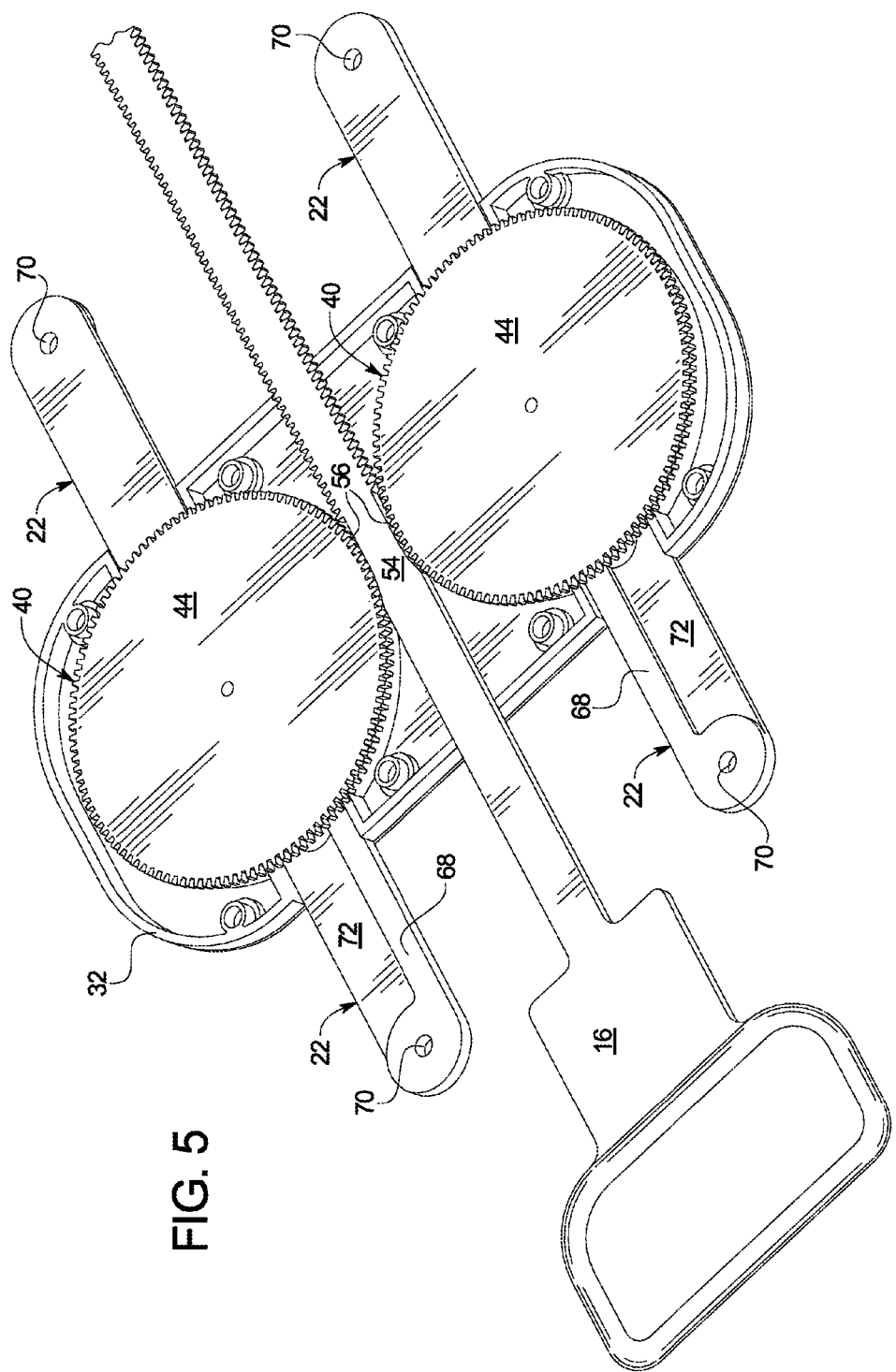
FIG. 5 is a perspective view of the adjustment assembly for the gear-on-gear embodiment of FIG. 1, which has been flipped from the view of FIG. 4 to show the front faces of the larger gears of the gear sets.

FIGS. 3 to 5 illustrate that the inner, smaller rotational gears 42 each communicate with a pair of retraction rack gears 22. The retraction rack gears 22 are in one embodiment about 0.115 inch to 0.188 inch (2.9 to 4.8 mm) thick at their thick portions and about 0.063 inch (1.6 mm) thick at their thin portions. Rack gears 22 can be made from any of the materials described herein. As seen best in FIG. 7, retraction rack gears 22 each have a stepped thickness so that when mated, at least a portion of the linear gear teeth 68 of each rack 22 lie in the same plane. In particular, each rack gear 22 has a thicker portion 66 that defines linear gear teach 68 (also forming one side wall of a slot 74) and a side panel mounting hole 70. Each rack gear 22 also has a thinner portion 72 defining the remainder of slot 74 and receiving the linear gear teeth 68 of a mating rack gear.

Figure 6:
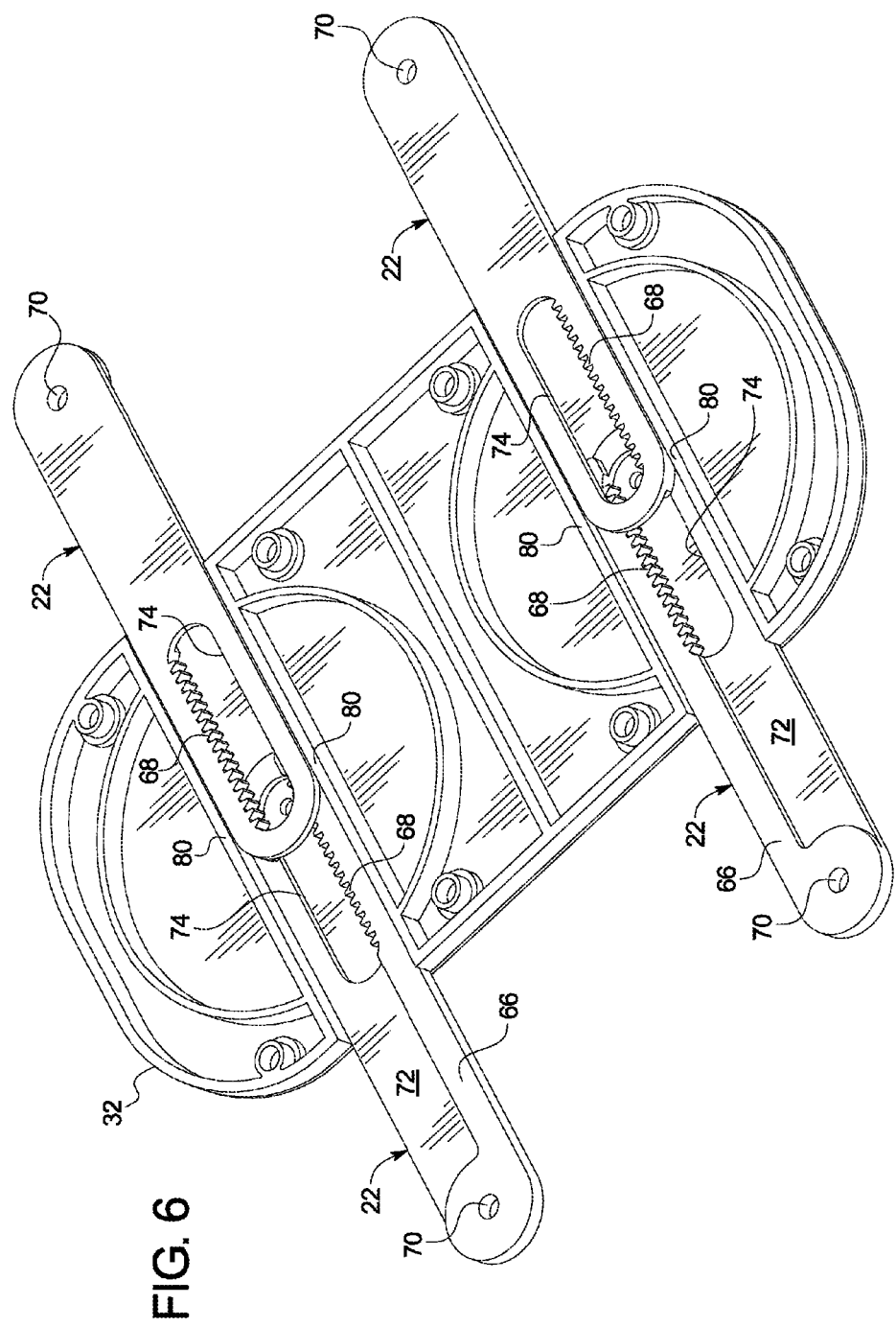
FIG. 6 is the perspective view of FIG. 5 with the gear sets removed.
Figure 7:
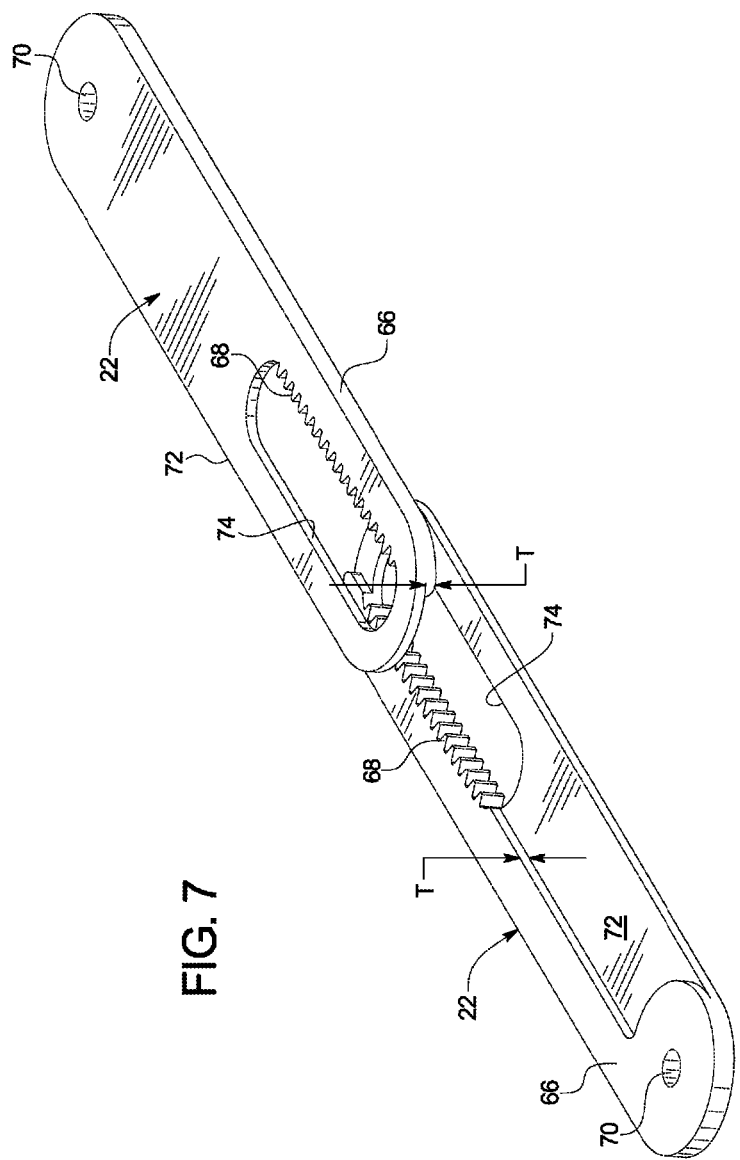
FIG. 7 is a perspective view of one embodiment of the translationally moving rack gears used with each gear-on-gear and gear-on-pulley version of the adjustable back braces of the present disclosure.

As seen best in FIGS. 6 and 7, when rack gears 22 are mated, slots 74 overlap each other by an amount that varies depending upon whether the rack gears have been pulled apart or pushed together. When pulled apart, the ends of the slots 74 opposite or furthest away from mounting holes 70 eventually reach smaller gears 42 (position of FIGS. 4, 6 and 7) at a fully expanded brace position and can no longer be moved apart. When pushed together, the opposite ends of slots 74 (near the middle of gears 22 and closer to mounting holes 70) of rack gears 22 eventually reach smaller gears 42 at a fully retracted or pushed-in brace position and can no longer be pushed together.

Thinner portion or step 72 allows rack gears 22 to be mated such that linear gears 68 lie in a same plane over a thickness T (FIG. 7) equal to the thickness of material removed (or not molded initially) to form thinner stepped portion 72, i.e., the difference in thickness between thicker portion 66 and thinner step 72. The height h (FIG. 3) of smaller gears 42 is in one embodiment at or about the distance of the added thicknesses of the thicker portion 66 and thinner step 72 of rack gears 22 to ensure that linear gears 68 of each gear 22 of a mated pair properly engage the smaller rotational gears 42. The radius of slots 74 and thus the distance that linear gears 68 are spaced apart from each other when rack gears 22 are mated is selected such that the teeth of linear gears 68 mesh appropriately with the gear teeth of smaller rotational gears 42.

Proximal ends 12p and 14p of side panels 12 and 14 each attach to the anterior or free ends of rack gears 22. To this end, the posterior end 12p and 14p of each side panel 12 and 14, respectively, includes a tough but flexible sew-on tab reinforcement 76, which defines attachment holes 78 (FIG. 1) for mating with side panel mounting holes 70 holes formed in the distal ends of the rack gears 22. The aligned holes can receive rivets, screws or other suitable fasteners for securing proximal ends 12p and 14p of side panels 12 and 14 to rack gears 22 and thus to adjuster assembly 20. Tab reinforcements 76 are made of a flexible but tough material, such as a flexible acrylic thermal plastic or low density polyurethane ("LDPE") or other stitchable material or fabric.

Pulling handle portion 16 of adjuster strap or actuator 50 outwardly, away from gear housing 30, causes larger gears 44 and thus smaller gears 42 (e.g., at a five to one mechanical advantage ratio) to rotate, such that rack gears 22 retract translationally inwardly towards a center of gear housing 30 (roughly coextensive with wearer's spine). Rack gears 22 in turn pull the side panels 12 and 14 inwards towards gear housing 30 and thus tighten brace 10. FIG. 6 shows that back plate 32 includes or defines walls 80 that form linear channels within which rack gears 22 are guided while moving translationally inwardly or outwardly.

Side panels 12 and 14 are each made of a flexible mesh trampoline material in one embodiment. As illustrated in FIG. 1, side panel 14 has a channel 82 formed by two stiffer polyester films (not seen) laid back-to-back and sealed at their edges. The two polyester film strips are, in one embodiment, exactly the same size and shape as a pile fabric strip 84, which is stitched together with the polyester strips. That is, the plastic films and pile strip of channel 82 are stacked on top of one another in the following order: the polyester film, the second polyester film and the pile strip 84. The stack or channel 82 is then sewn on three sides of its perimeter to the trampoline mesh material of side panel 14, such that the pile material faces outwardly to allow various positions for a mating item having a hook material to be attached removeably to panel 14. An oval hole 83 is formed at the proximal end of the pile strip 84 into which the rack gear portion 52 of the adjustor strip 50 is inserted, such that the rack gear portion is held out of the way and in a sheathed condition. The resulting channel 82 encases rack gear portion 52 and distal end 58 of the adjuster strap 50 between the polyester strips for smooth adjustment, so that actuator 50 is contained and forced to wrap around the waist of the wearer.

Mesh trampoline side panel 12 has its own pile strip 86 sewn down its middle. Pile strip 86 accepts and holds a hook material 88 placed on the underside of the handle portion 16 of adjuster strap 50 at a position that the wearer has pulled strap 50 to tension the brace 10 at a desired level.

Right panel 14 (viewed from the back of the wearer in FIG. 1) extends from the right of the wearer's spine, around to the front of the wearer's waist with its anterior or distal end 14a extending slightly past the midline of the wearer's front. The left-hand panel 12 extends from the left of the wearers spine (viewed from the back of the wearer in FIG. 1), around to the front of the patient's waist with its anterior or distal end 12a extending slightly past the midline of the wearer's front, such that the anterior or distal ends 12a and 14a of panels 12 and 14 can be attached to each other. The distal or anterior end of one of the side panels 12 and 14 has a hook material sewn to the underside of its mesh trampoline material to engage a pile surface sewn to the top surface of the distal or anterior end of the trampoline material of the other side panel 14 or 12, respectively.

As seen in FIG. 1, in one embodiment, for any of the braces described herein, right panel 14 can loop over the outside of left panel 12 (viewed from the back of the wearer in FIG. 1). The outside of the very end 12a of the left panel 12 has hook material that extends the entire width (extending vertically along the user) of the left panel 12, and which extends inwardly (to the left in FIG. 1) from the very end 12a along the outside of left panel 12 for a first distance, such as two inches (5.08 centimeters). The hook material is followed by a section of pile material that likewise that extends the entire width (extending vertically along the user) of the left panel 12, and which extends further inwardly (to the left in FIG. 1) from the end of the hook material section along the outside of left panel 12 for a second distance, such as six inches (15.2 centimeters). The exact same arrangement, e.g., two inch (5.08 centimeter) hook material from end 14a followed by six inch (15.2 centimeter) pile material from hook material, is placed on the inside of right panel 14. The arrangement allows four inches (10.2 centimeters) of adjustment around the user's waste (assuming all two inches of both hook sections are applied to mating pile sections). The adjustment is a brace positioning adjustment, while the adjustment provided by adjuster assembly 20 is a tensioning adjustment.

When the adjusting handle 16 is in its most retracted (pushed-in) position (such that the retraction rack gears 22 are in their most extended position and the waist circumference of the panels is at its maximum), the rack gear portion 52 of adjuster strap 50 extends its furthest into channel 82 formed by the polyester strips beneath the pile strip 84 on side panel 14. After the wearer lifts handle portion 16 from pile strip 86 on side panel 12 and pulls the handle portion 16 to the left (viewed from the back of the wearer in FIG. 1), rack gears 22 are caused to translate inwardly and pull side panels 12 and 14 closer to gear housing 30 to adjust tension on the brace to a desired level. The wearer then presses handle portion 16 back onto the pile strip 86 of side panel 12 to hold brace 10 in an adjusted and tensioned position. To loosen brace 10, the wearer releases handle portion 16 from pile strip 86. The tension on brace 10 will be released, such that brace 10 will tend to loosen itself. If need be, the wearer can push handle portion 16 inwardly or extend the wearer's belly to loosen brace 10.

Multiple Gear-on-Pulley

Referring now to FIGS. 8 to 11, a second primary embodiment of the present disclosure, namely, a, multiple gear-on-pulley adjustable brace 110 is illustrated. With brace 110, the larger gears 44 of gear-on-gear brace 10 are replaced with pulleys 144. The rack gear portion 52 of the adjusting strap 50 of brace 10 is replaced with a cord 152 connected to an actuator 150. Cord 152 also attaches to pulleys 144. Braces 10 and 110 are otherwise similar. The two equivalent diameter pulleys 144 provide a mechanical advantage, such as a five-to-one mechanical advantage. Cord 152 is affixed to each of pulleys 144 and is wrapped around the pulleys making, e.g., one-half to three revolutions, and in one embodiment 1.5 turns, to allow sufficient cord length for the complete translational adjustment of rack gears 22. Cord 152 then runs from large pulleys 144 to a balancer pulley 160 located on the adjuster handle 116. Adjuster handle, like handle portion 16, has hook material 88 located on its opposing surface for attachment to pile strip 86 located on side panel 12. Pulleys 444 can be made of any of the materials described above for gear set 40 or the retraction rack gears 22. Likewise, any of the components of adjustable brace 110 may be made of any of the materials and methods discussed above for brace 10.

Cord 152 for each pulley 144 is trapped inside housing 130 in the same manner as described below for cord 252 and the single pulley 244 of the single gear-on-pulley brace 210. Each pulley 144 includes a slotted aperture 146 that allows cord 152 to have its enlarged end (FIGS. 16 to 18) pulled against the back panel side of pulleys 144 and then to extend radially outwardly within the thickness of pulleys 144 on the front panel side of pulleys 144. Cord 152 then continues around the outside of pulleys 144 for a desired circumferential distance before radiusing out of housing 130, to balance pulley 160, via a pair of apertures 164 formed in front or outside panel 134. Back or inside panel 132 defines or includes circular walls 138 (FIG. 10) that help to trap cord 152 in place around the outside of pulleys 144 when panel 134 is attached to panel 132 to form housing 130.

Brace 110 includes an adjuster assembly 120 having a housing 130 made of any of the materials discussed above for housing 30. Housing 130 includes a back panel 132 (FIG. 9, located closer to the wearer when brace 110 is worn and having through-holes for mounting screens) that is bolted to a front panel 134 (FIG. 11, facing away from the wearer when worn and including threaded holes or inserts 48 for threadingly receiving fastening screws). Housing 132 includes or defines walls 80 (FIG. 10) forming channels for receiving and guiding rack gears 22. Housing 134 likewise includes or defines linear walls 62 forming a channel for receiving and guiding cord 152 and circular walls 64 (FIG. 11) for accepting and orienting large pulleys 144.

Figure 8:
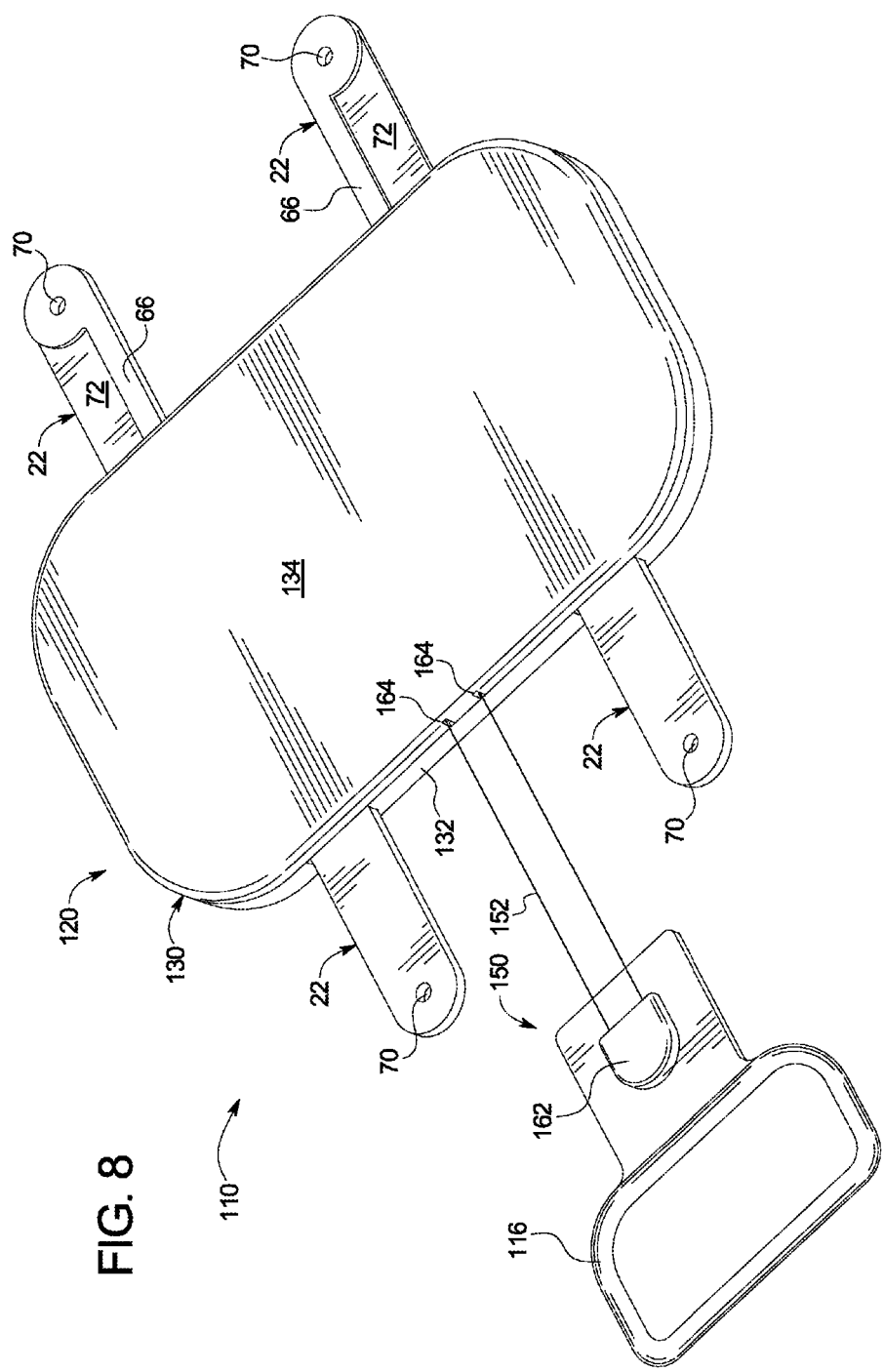
FIG. 8 is a front perspective view of one embodiment of an assembled adjustment assembly for the gear-on-pulley version of the adjustable back brace of the present disclosure.
Figure 11:
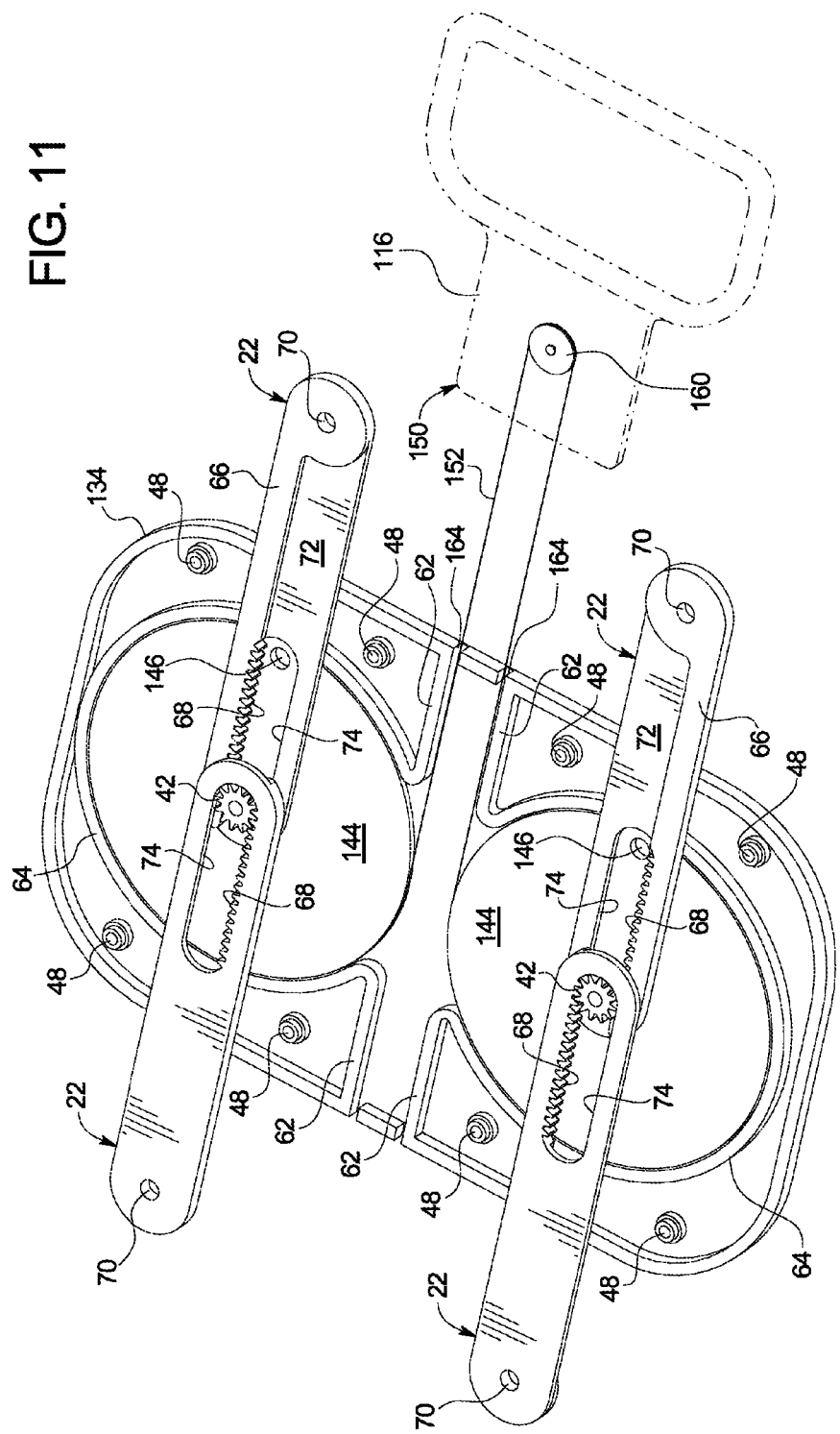
FIG. 11 is the rear perspective view of FIG. 9 with the back plate removed and the handle portion of the actuator shown in phantom to illustrate the gear/pulley sets and balancer pulley, respectively.
Figure 12:
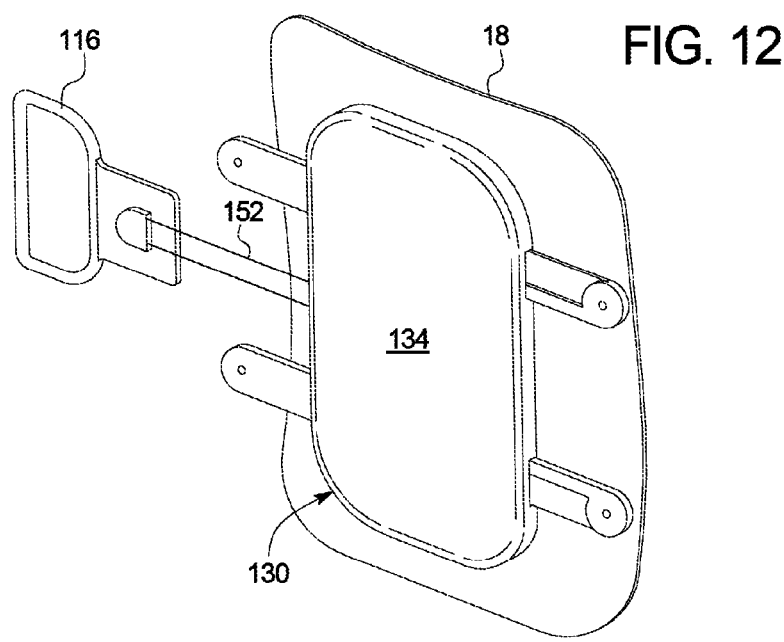
FIG. 12 is a perspective view of the assembled gear-on-pulley version of the adjustment assembly in operable position with an accessory back plate support.

FIGS. 8 and 12 show that handle portion 116 of actuator 150 includes a balancer pulley cover 162 housing balancer pulley 160 (FIGS. 10 and 11) on the outside surface of handle portion 116 (opposing the side with hook material 88). Balancer pulley 160 allows for the coning of brace 110, which occurs when the user's body causes the brace when worn to form a slight cone shape as opposed to a perfect cylinder or ellipse around the user. For example, the user's hips may be wider than the user's lower back, which will cause brace 110 to widen as it extends from top to bottom. Or, the user's chest may be wider than the user's lower back, which may cause brace 110 to narrow as it extends from top to bottom. Coning may be prevalent enough to cause the upper rack gears 22 to be adjusted differently than the lower rack gears 22. Balancer pulley 160 (as do the slight cutouts or indents 56 of transition portion 54 of strap 50 above) helps to allow for such different rack gear adjustment to occur.

Balancer pulley 160 also allows the force applied by the wearer's pull to be optimally at least approximately parallel to the linear movement of rack gears 22 regardless of whether or not handle portion 116 is centered horizontally relative to housing 130. Cord 152 is made of a tensially strong cable or wire, such as wire used for sports rackets or fishing wire.

Figure 9:
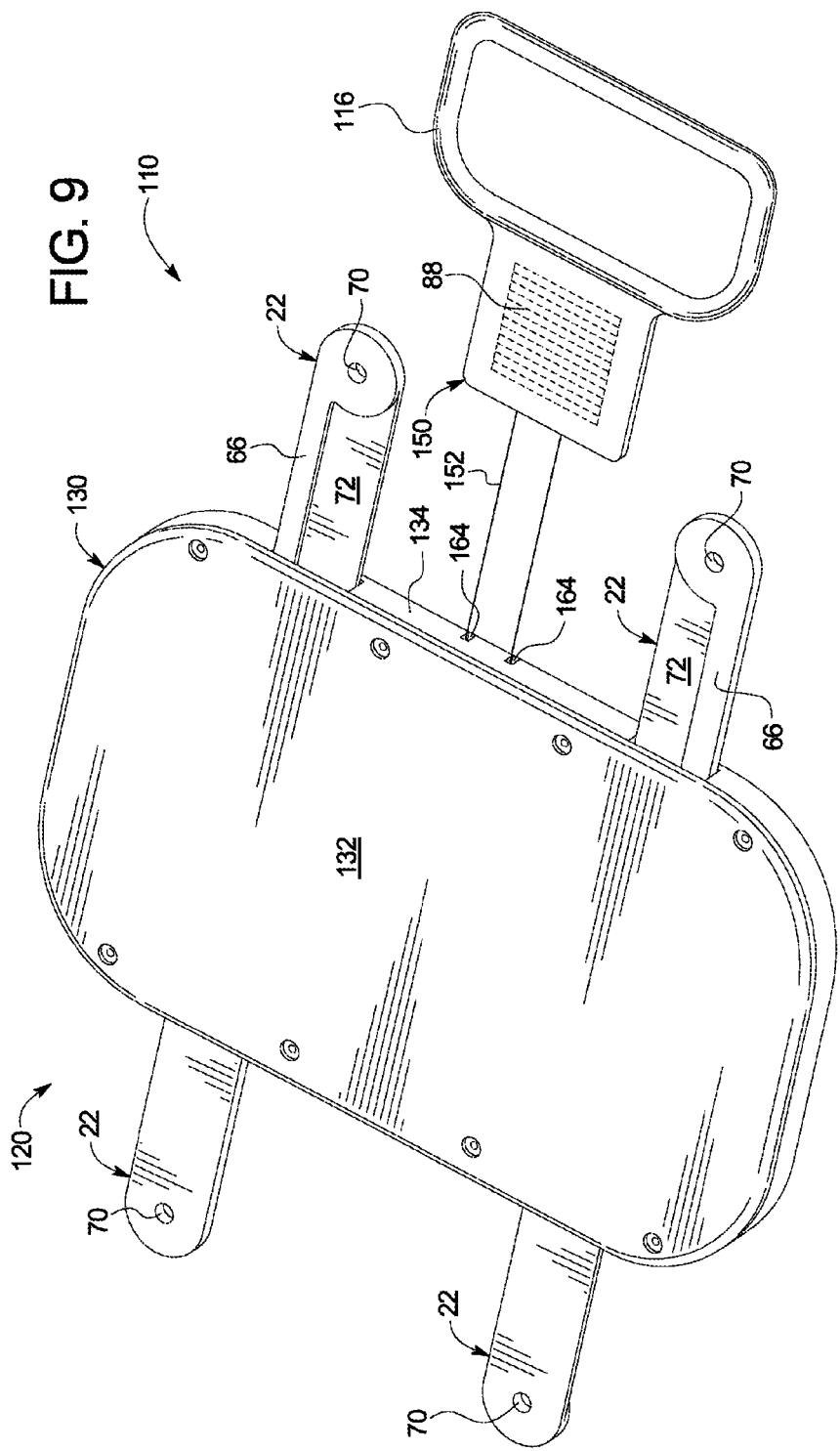
FIG. 9 is a rear perspective view of one embodiment of an assembled adjustment assembly for the gear-on-pulley version of the adjustable back brace of the present disclosure.
Figure 13:
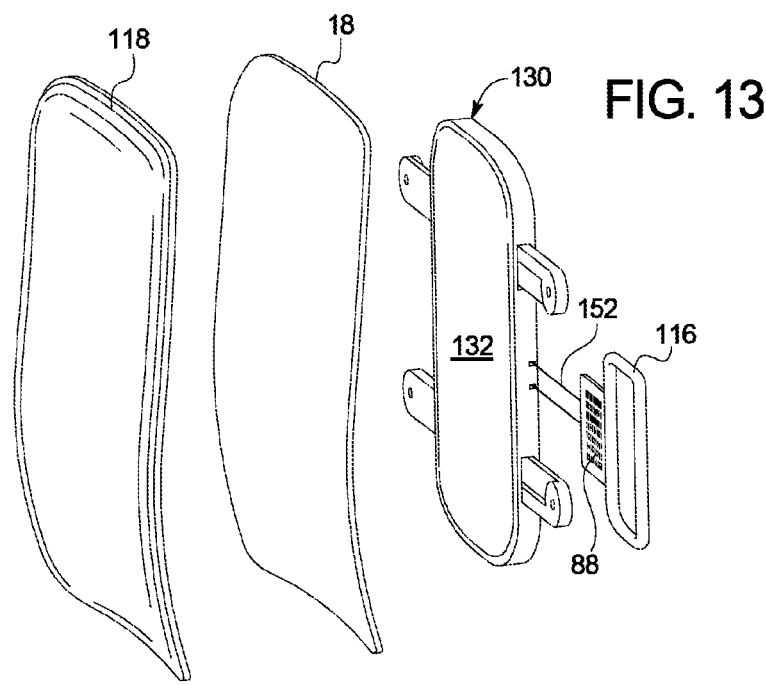
FIG. 13 is an exploded view of the assembled gear-on-pulley version of the adjustment assembly in operable position with an accessory back plate support and inflatable pad.

Side panels 12 and 14 are the same as above for brace 10, except that the right side panel 14 (as seen in FIG. 1) does not need channel 82 to receive a rack gear portion 52 of the adjuster 150, which does not exist with the gear-on-pulley brace 110. Again, as seen at FIGS. 9 and 13, adjuster handle 116 includes a hook material 88 placed on its underside, such that the wearer can press hook material 88 onto pile strip 86 located on the side panel 12 to lock the brace in a desired tensioned position.

Gear-on-pulley brace 110 includes the inner and outer rack gears 22 discussed above for gear-on-gear brace 10, which again operate in geared relation with small central gears 42, here located at the center of each large pulley 144. The rack gears 22 adjust the panels in the same manner as described above for gear-on-gear brace 10. Pulling the adjusting handle 116 outwardly (to the left as viewed in FIG. 1) pulls the cable or cord 152 away from gear housing 130 and causes the two large pulleys to turn so as to retract the four rack gears and tighten the side panels 12 and 14. To loosen brace 110, the user unhooks handle portion 116 from pile strip 86 and allows the tension to be released to a new setting (at which the wearer re-hooks handle 116 to pile strip 86) or to remove brace 110 completely.

Accessory Items

Each brace described herein, including gear-on-gear brace 10 and gear-on-pulley braces 110 and 210, is operable with various accessories. FIGS. 12 and 13, for example, show brace 110 being used with an optional back plate 18, which may be attached to gear-on-pulley housing 130 or gear-on-gear housing 30 (or housing 230 discussed below) via a suitable releasable means, such as a snap-fit, slide engagement or hook and pile attachment. Alternatively, back plate 18 is completely separate from housing 30 or 130 (or 230) and is held in a place by the tensioned brace 10 or 110 (or 210). In either case, back plate 118 can be rotated 180 degrees (turned upside down) relative to the brace to allow the same brace to be worn by the wearer in either a right-handed or left-handed operating position. Alternatively, if back plate 18 is permanently affixed to the housing, it is contemplated to make right-handed or left-handed versions of brace 10 and 110 (and 210).

Optional back plate 18 can have a shape contoured for the wearer's spine as seen in FIGS. 12 and 13 or simply be flat and be made of any of the materials described herein. If flat, then the right-handed or left-handed options discussed above are rendered moot or not needed. In any case, back plate 18 provides additional support for the wearer's back and spine. FIG. 13 shows that detachable back plate 18 can carry an accessory pad or an air bladder 118 to aid in padding or conforming brace 10 or 110 (or 210) to the lumbar area of a wearer's back. If back plate 18 is not provided, the pads or air bladder 118 can alternatively be attached directly to the gear-on-pulley housing 130 (or 230) or gear-on-gear housing 30 or used loosely but directly with the housing.

Figure 14:
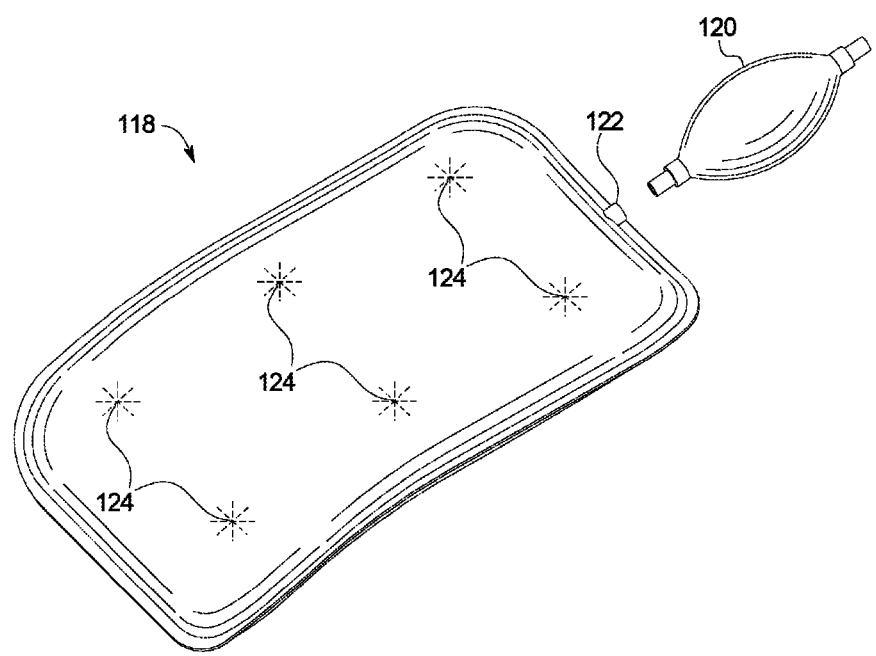
FIG. 14 is a perspective view of one embodiment of an inflatable pad accessory for the adjustable back brace of the present disclosure.

FIG. 14 illustrates that air bladder 118 can be operated with a hand air pump 120 that the wearer couples to an inlet port 122 of the bladder 118. The wearer squeezes hand pump 120 a number of times until the air bladder is filled to a pressure desired by the user. Air bladder 118 is in one embodiment made of a flexible and weldable material, such as vinyl or polyurethane. Weld spots or dimples 124 form a pattern that controls how thick bladder 118 can become when inflated. If it is desired for bladder 118 to be thicker overall or in certain areas, weld spots or dimples 124 are spaced farther apart, creating more open room in between dimples 124 to receive pumped air. If it is desired for bladder to be thinner overall or in certain areas, weld spots or dimples 124 are spaced more closely together, creating less open room for air from pump 120 to spread the walls of bladder 118 apart. Either or both of the back plate 18 and the air bladder 118 can be used alternatively at the front or anterior section of the wearer.

Single Gear-on-Pulley

Referring now to FIGS. 15 to 18, one embodiment of a single gear-on-pulley adjustable back brace is illustrated by brace 210. It should be appreciated that the present inventors contemplated a single gear-on-pulley or single gear-on-gear brace at and before the time of the filing of the priority provisional application. This should be readily apparent from at least paragraphs [0021] to [0023] of U.S. provisional patent Application No. 61/245,922.

Figure 16:
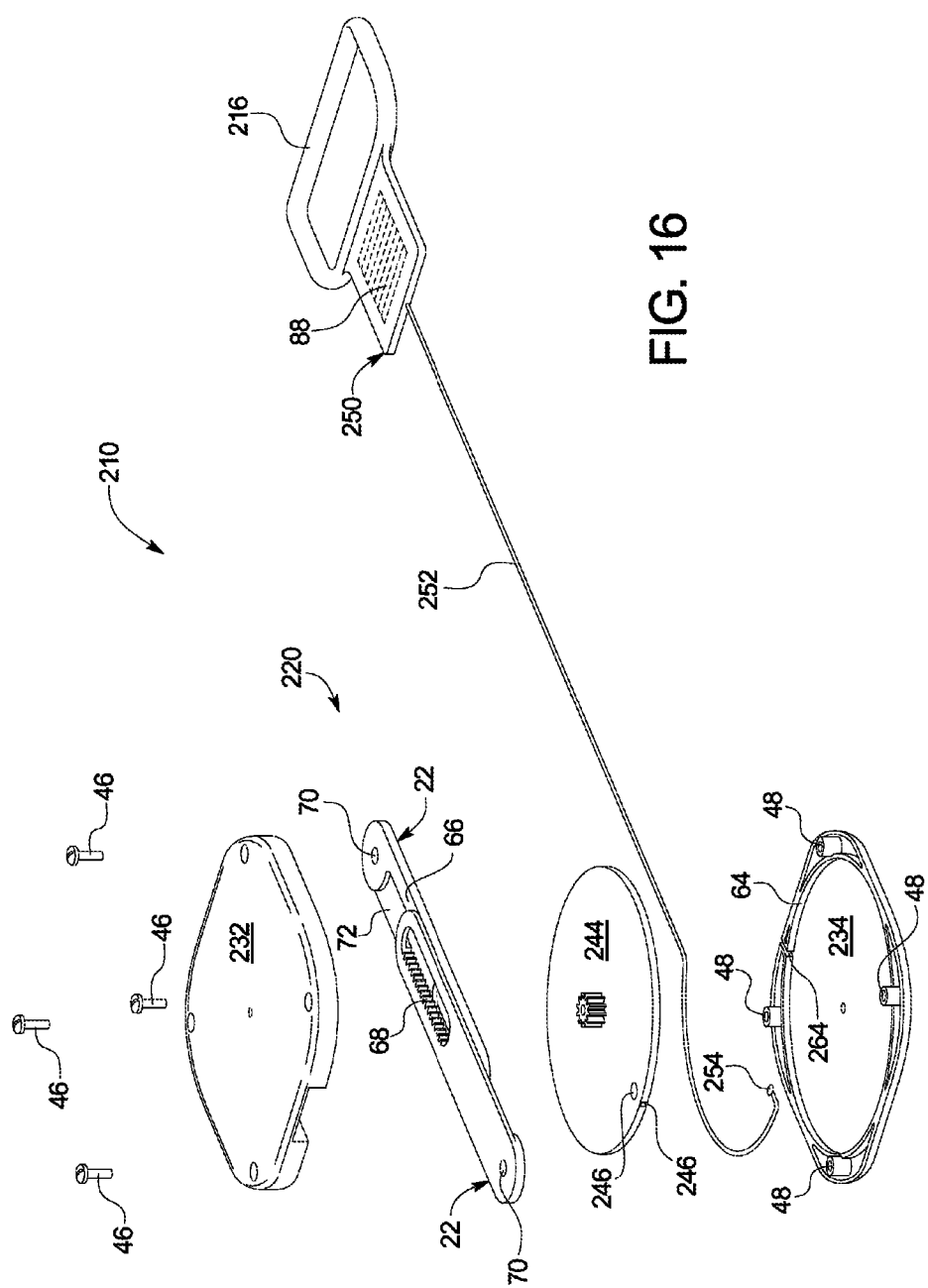
FIG. 16 is a first exploded perspective view (minus flexible side panels) of one embodiment of a single gear-on-pulley version of the adjustable back brace of the present disclosure.
Figure 17:
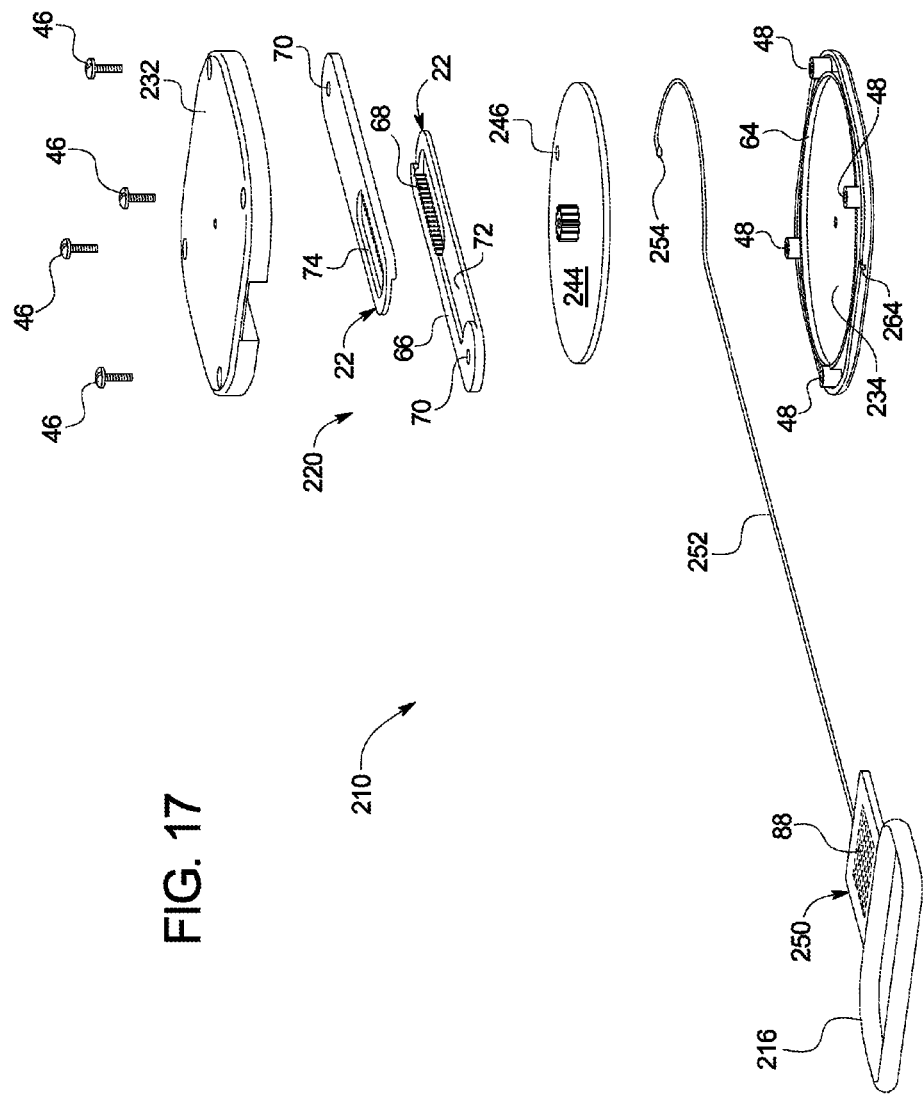
FIG. 17 is a second exploded perspective view (minus flexible side panels) of one embodiment of a single gear-on-pulley version of the adjustable back brace of the present disclosure.

With brace 210, the larger gears 44 of gear-on-gear brace 10 are replaced here with a single pulley 244. The single equivalent diameter pulley 244 provides a mechanical advantage, such as a five-to-one mechanical advantage. The rack gear portion 52 of the adjusting strap 50 of brace 10 is replaced with a cord 252 connected to an actuator 250. Cord 252 also attaches to single pulley 244. As seen in FIGS. 16 to 18, cord 252 in one embodiment includes a knotted or enlarged end 254 that is trapped through an aperture 246 in pulley 244 on the geared side of single pulley 244 (FIGS. 16 and 17). Cord 252 then extends radially on the non-geared side of pulley 244 (FIG. 18) through a groove or slot of aperture 246 out to the edge circumference of single pulley 244.

Cord 252 is affixed to pulley 244 at aperture 246 as described above and is wrapped around the pulley making, e.g., one-half to three, revolutions to obtain a to allow the length of cord 252 to be sufficient for full adjustment of rack gears 22. Cord 252 then runs from pulley 244 directly to an adjuster handle 216. Here, because two pulleys are not provided, only a single cord runs to handle 216, such that the balancer pulley 160 located on the adjuster handle 116 of brace 110 is not needed. Adjuster handle 216, like handles 16 and 116, has hook material 88 located on its opposing surface for attachment to pile strip 86 located on side panel 12. Pulley 244 can be made of any of the materials described above for gear set 40 or the retraction rack gears 22.

Brace 210 includes an adjuster assembly 220 having a housing 230 made of any of the materials discussed above for housing 30. Housing 230 includes a back panel 232 (located closer to the wearer when brace 210 is worn and having through-holes for mounting screws) that is bolted to a front panel 234 (facing away from the wearer when worn and including threaded holes or inserts 48 (FIGS. 16 and 17) for threadingly receiving fastening screws. Back panel 232 includes or defines walls 80 (FIG. 18) forming a channel for receiving and guiding a set of rack gears. Front panel 234 includes or defines a circular wall 64 (FIGS. 16 and 17) for accepting and orienting pulley 244. Front panel 234 also includes or defines an opening 264 in its side that allows cord 252 to extend into and out of front panel 234 and thus housing 230.

In one embodiment, circular wall 64 of front panel 234 is sized to have a diameter that is slightly larger than the diameter of pulley 244, so that cord 252 is forced to extend around the outside of pulley 244 and inside the slightly larger diameter circular wall 64. The slotted portion of aperture 246 (FIG. 18) enables cord 252 to extend from the outer diameter of pulley 244 radially inward a short distance within the thickness of pulley 244, so that pulley 244 can lay perfectly flat against front panel 234. In this manner, cord 252 can be inserted from the back panel 232 side of pulley 244 through aperture 246 until enlarged end 254 of cord 252 is pulled against the panel 232 side of pulley 244. The cord is then pulled though the slotted portion of aperture 246 and around the outside of pulley 244. If desired, the outer edge of pulley 244 can be slotted to trap cord 252. In the illustrated embodiment a circular wall 238 formed with back panel 232 sits directly over cord 252, trapping the cord in place when back panel 232 is secured to front panel 234.

In one embodiment, adjustable brace 210 in use is oriented such that hook material 88 attaches to pile strip 86 (FIG. 1) located on side panel 12. Cord 252 is wound over the top of pulley 244 as worn by the user and opening 264 in front panel 234 is located such that cord extends from housing 230 slightly above a horizontal centerline of housing 230 as worn by the user. Such structure relaxes the tightness of the radius that cord 252 has to make in transitioning from its circular shape around the diameter of pulley 244 to its horizontal extension to the handle 216 of actuator 250.

Side panels 12 and 14 for adjustable brace 210 are the same as above for brace 10, except that the right side panel 14 (as seen in FIG. 1) does not need channel 82 to receive a rack gear portion 52 of the adjuster 150, which does not exist with the gear-on-pulley brace 210. Also, side panels 12 and 14 attach to only a single, e.g., centralized, rack gear as opposed to attaching to upper and lower rack gears as is done with braces 10 and 110. Here, proximal ends 12p and 14p of side panels 12 and 14 (FIG. 1) each attach to the distal or free end of a single rack gear 22. To this end, the proximal end 12p and 14p of each side panel 12 and 14, respectively, includes a tough but flexible sew-on tab reinforcement 76, which defines an attachment hole 78 located roughly horizontally centrally on the panels for mating with a side panel mounting hole 70 hole formed in the distal end of each of the rack gears 22, which resides roughly horizontally centrally with respect to housing 230. The centralized force vector of single gear-on-pulley brace 210 (and the single gear-on-gear brace discussed below) helps to compensate for the user caused coning effect discussed above. The aligned holes can receive rivets, screws or other suitable fasteners for securing proximal ends 12p and 14p of side panels 12 and 14 to rack gears 22 and thus to adjuster assembly 220. Tab reinforcements 76 can again be made of a flexible but tough material, such as a flexible acrylic thermal plastic or low density polyurethane ("LDPE") or other stitchable material or fabric.

Figure 15:
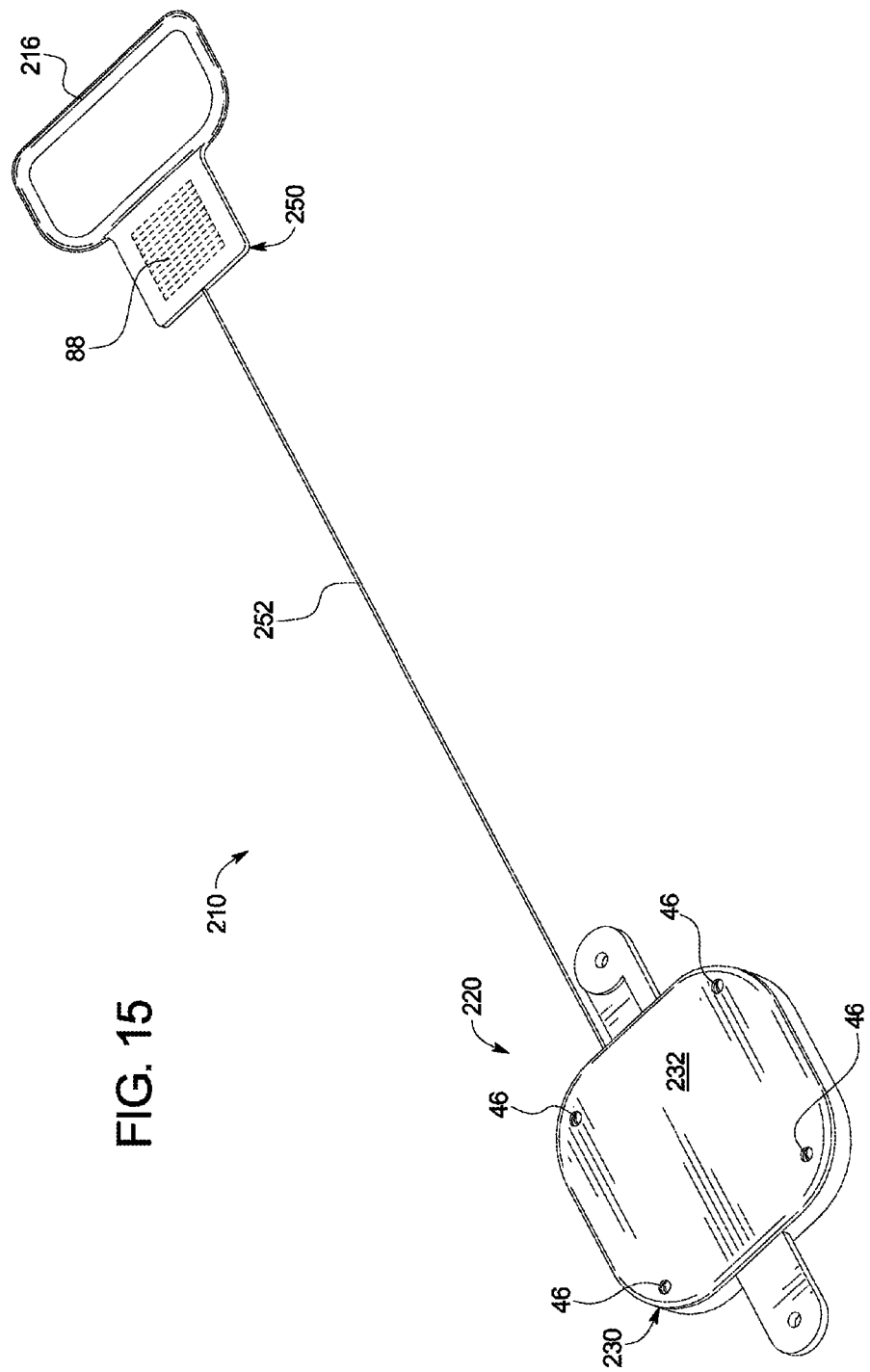
FIG. 15 is an assembled perspective view (minus flexible side panels) adjustable of one embodiment of a single gear-on-pulley version of the adjustable back brace of the present disclosure.

Single gear-on-pulley brace 210 includes one set of inner and outer rack gears 22, which again operate in geared relation with a single small central gear 42, here located at the center of large pulley 244 and at the approximate center of housing 230. Rack gears 22 adjust side panels 12 and 14 in the same manner as described above for gear-on-gear brace 10 and multiple gear-on-pulley brace 110. Again, as seen at FIGS. 15 to 17, adjuster handle 216 includes a hook material 88 placed on its underside, such that the wearer can press hook material 88 onto pile strip 86 located on side panel 12 to lock the brace in a desired tensioned position. Pulling the adjusting handle 216 outwardly (to the left as viewed in FIG. 1) pulls the cable or cord 252 away from gear housing 230 and causes single pulley 244 to turn so as to retract the two rack gears 22 and tighten the side panels 12 and 14. To loosen brace 210, the user unhooks handle portion 216 from pile strip 86 and allows the tension to be released to a new setting (at which the wearer re-hooks handle 216 to pile strip 86) or to remove brace 210 completely.

Adjustable brace 210 is operable with any of the accessory items discussed herein and in the same manner as with either of braces 10 or 110. Any of the components of adjustable brace 210 may be made of any of the materials and Methods discussed above for braces 10 and 110.

Single Gear-on-Gear

While brace 110 has been described using a single pulley 244, it is also contemplated to provide a single gear-on-gear version of the adjustable back brace. Viewing FIG. 1, is contemplated to eliminate the upper gear set 40 and associated rack gears 22. The remaining lower gear set 40 and rack gear portion 52 are shifted upwardly so that the center of lower gear set 40 resides roughly at the horizontal center of housing 30. In this manner, the remaining, now centralized, rack gears 22 pull at the horizontal center of each of side panels in same manner as do the rack gears 22 of adjustable brace 210.

Channel 82 and pile strips 84 and 86 are likewise shifted up to mate with shifted rack gear portion 52. A smaller follower rotary gear (not illustrated) is mated with the linear gear teeth along the top of rack gear portion 52 to force the lower linear gear teeth along the top of rack gear portion 52 into geared relationship with the larger gear 44 of the centralized gear set 40. The smaller rotary gear (not illustrated) is alternatively replaced with a guide wall (not illustrated) that serves a similar role as guide walls 62 (FIG. 4). The operation of adjuster strap 50 and the tightening and loosening of the single gear-on-gear version of the adjustable back brace is the same as for dual gear-on-gear brace 10. As with all other braces described herein, any of the accessories described herein may be used in combination with the single gear-on-gear version of the adjustable back brace, the components of which may be made of any of the materials and methods discussed herein.

ADDITIONAL ASPECTS OF THE PRESENT DISCLOSURE

Aspects of the subject matter described herein may be useful alone or in combination one or more other aspect described herein. Without limiting the foregoing description, in a first aspect of the present disclosure, an adjustable orthopedic back brace includes: a first side panel having a distal end and a proximal end; a second side panel having a distal end and a proximal end; a rotating gear in geared communication with a first rack gear, the first rack gear connected to the proximal end of the first side panel, the rotating gear in geared communication with a second rack gear, the second rack gear connected to the proximal end of the second side panel; a mechanical advantage member rotatable with and providing mechanical advantage for the rotating gear; and an actuator connected operably to the mechanical advantage member for turning the member and the rotating gear to cause a translational movement of (i) the first rack gear and the first side panel and (ii) the second rack gear and the second side panel.

In accordance with a second aspect of the present disclosure, which may be used in combination with the first aspect, the rotating gear is a first rotating gear, the mechanical advantage member is a first mechanical advantage member, and which includes (a) a second rotating gear in geared communication with a third rack gear, the third rack gear connected to the proximal end of the first side panel, the second rotating gear in geared communication with a forth rack gear, the forth rack gear connected to the proximal end of the second side panel; (b) a second mechanical advantage member rotatable with and providing mechanical advantage for the second rotating gear; and (c) the actuator connected operably to the first and second mechanical advantages member to cause a translational movement of (i) the first rack gear, the third rack gear and the first side panel and (ii) the second rack gear, the forth rack gear and the second side panel.

In accordance with a third aspect of the present disclosure, which may be used in combination with any one or more of the preceding aspects, the mechanical advantage member includes a larger rotating gear, the actuator including a rack gear portion operable with the larger rotating gear.

In accordance with a fourth aspect of the present disclosure, which may be used in combination with any one or more of the preceding aspects, the mechanical advantage member is connected to or integral with the rotating gear.

In accordance with a fifth aspect of the present disclosure, which may be used in combination with any one or more of the preceding aspects, the mechanical advantage member includes a pulley.

In accordance with a sixth aspect of the present disclosure, which may be used in combination with the fifth aspect, the actuator includes a cord connected to the pulley.

In accordance with a seventh aspect of the present disclosure, which may be used in combination with any one or more of the preceding aspects, the actuator includes a handle configured to be secured releasably to one of the first and second side panels.

In accordance with an eighth aspect of the present disclosure, which may be used in combination with any one or more of the preceding aspects, the distal ends of the first and second side panels are configured to be releasable secured together.

In accordance with a ninth aspect of the present disclosure, which may be used in combination with any one or more of the preceding aspects, an adjustable orthopedic back brace includes: a first side panel having a distal end and a proximal end; a second side panel having a distal end and a proximal end; a first rotating gear in geared communication with a first rack gear, the first rack gear connected to the proximal end of the first side panel, the first rotating gear in geared communication with a second rack gear, the second rack gear connected to the proximal end of the second side panel: a second rotating gear in geared communication with a third rack gear, the third rack gear connected to the proximal end of the first side panel, the second rotating gear in geared communication with a forth rack gear, the forth rack gear connected to the proximal end of the second side panel; a first mechanical advantage member rotatable with and providing mechanical advantage for the first rotating gear; a second mechanical advantage member rotatable with and providing mechanical advantage for the second rotating gear; and an actuator connected operably to the first and second mechanical advantage members for turning the first and second members and the corresponding first and second rotating gears to cause a translational movement of (i) the first rack gear, the third rack gear and the first side panel and (ii) the second rack gear, the forth rack gear and the second side panel.

In accordance with a tenth aspect of the present disclosure, which may be used with any one or more of the preceding aspects in combination with the ninth aspect, the first and second mechanical advantage members and the first and second rotating gears are located in a common housing.

In accordance with an eleventh aspect of the present disclosure, which may be used with any one or more of the preceding aspects in combination with the ninth aspect, at least one of the first and second mechanical advantage members is formed with the corresponding first and second rotating gear.

In accordance with a twelfth aspect of the present disclosure, which may be used with any one or more of the preceding aspects in combination with the ninth aspect, at lease one of (i) the first and second rack gears and (ii) the third and forth rack gears are mated such that at least a portion of their respective gear teeth lie in a common plane with the respective first or second rotating gear.

In accordance with a thirteenth aspect of the present disclosure, which may be used with any one or more of the preceding aspects in combination with the ninth aspect, the at least one mated set of rack gears has a stepped thickness such that the rack gears mate in an overlapping manner.

In accordance with a fourteenth aspect of the present disclosure, which may be used with any one or more of the preceding aspects in combination with the ninth aspect, at least one of (i) the first and second rack gears and (ii) the third and forth rack gears are mated such that their respective gear teeth lie on opposing sides of the respective first or second rotating gear.

In accordance with a fifteenth aspect of the present disclosure, which may be used with any one or more of the preceding aspects in combination with the ninth aspect, the adjustable orthopedic back brace includes at least one stationary guide for guiding translational movement of at least one of the first, second, third and forth rack gears.

In accordance with a sixteenth aspect of the present disclosure, which may be used with any one or more of the preceding aspects in combination with the ninth aspect, at least one of the first, second, third and forth rack gears defines a slot and has gear teeth formed on a wall defining the slot.

In accordance with a seventeenth aspect of the present disclosure, which may be used with any one or more of the preceding aspects in combination with the ninth aspect, the actuator includes a handle portion for manual movement of the actuator, and wherein the handle portion is configured to releasably attach to one of the first and second side panels to hold the rack gears at a desired position.

In accordance with an eighteenth aspect of the present disclosure, which may be used with any one or more of the preceding aspects in combination with the ninth aspect, one of the first and second side panels includes a channel for receiving and routing a mechanical advantage member actuation portion of the actuator.

In accordance with a nineteenth aspect of the present disclosure, which may be used with any one or more of the preceding aspects in combination with the ninth aspect, at least one of the first and second mechanical advantage members includes a larger rotating gear, the actuator including a rack gear portion operable with the at least one larger rotating gear.

In accordance with a twentieth aspect of the present disclosure, which may be used with any one or more of the preceding aspects in combination with the nineteenth aspect, the actuator includes an indented portion adjacent the rack gear portion for holding the actuator in a fully retracted position against the at least one larger rotating gear.

In accordance with a twenty-first aspect of the present disclosure, which may be used with any one or more of the preceding aspects in combination with the ninth aspect, at least one of the first and second mechanical advantage members includes a pulley, and wherein the actuator includes a cord attached to the at least one pulley, the cord running to a handle portion of the actuator.

In accordance with a twenty-second aspect of the present disclosure, which may be used with any one or more of the preceding aspects in combination with the ninth aspect, the handle portion includes a balancer pulley for receiving the cord.

In accordance with a twenty-third aspect of the present disclosure, which may be used in combination with any one or more of the preceding aspects, an adjustable orthopedic back brace includes: a side panel having a distal end and a proximal end: a first rotating gear in geared communication with a first rack gear, the first rack gear connected to the proximal end of the side panel; a second rotating gear in geared communication with a second rack gear, the second rack gear connected to the proximal end of the first side panel; a first mechanical advantage member rotatable with and providing mechanical advantage for the first rotating gear; a second mechanical advantage member rotatable with and providing mechanical advantage for the second rotating gear; and an actuator connected operably to the first and second mechanical advantage members for turning the members and the corresponding first and second rotating gears to cause a translation movement of the first rack gear, the second rack gear and the side panel.

In accordance with a twenty-fourth aspect of the present disclosure, which may be used with any one or more of the preceding aspects in combination with the twenty-third aspect, the side panel is a first side panel, and which includes a second side panel having a distal end and a proximal end, the first rotating gear in geared communication additionally with a third rack gear, the third rack gear connected to the proximal end of the second side panel, the second rotating gear in geared communication additionally with a fourth rack gear, the fourth rack gear connected to the proximal end of the second side panel, the actuator connected operably to the first and second mechanical advantage members for turning the members and the corresponding first and second rotating gears to cause a translation movement of (i) the first rack gear, the second rack gear and the first side panel and (ii) the third rack gear, the forth rack gear and the second side panel.

In accordance with a twenty-fifth aspect of the present disclosure, which may be used with any one or more of the preceding aspects in combination with the twenty-third aspect, at least one of the first and second mechanical advantage members includes a larger rotating gear, the actuator including a rack gear portion operable with the at least one larger rotating gear.

In accordance with a twenty-sixth aspect of the present disclosure, which may be used with any one or more of the preceding aspects in combination with the twenty-third aspect, at least one of the mechanical advantage members includes a pulley.

In accordance with a twenty-seventh aspect of the present disclosure, any of the structure and functionality illustrated and described in connection with FIG. 1 may be used in combination with any one or more of the preceding aspects.

In accordance with a twenty-eighth aspect of the present disclosure, any of the structure and functionality illustrated and described in connection with FIG. 2 may be used in combination with any one or more of the preceding aspects.

In accordance with a twenty-ninth aspect of the present disclosure, any of the structure and functionality illustrated and described in connection with FIG. 3 may be used in combination with any one or more of the preceding aspects.

In accordance with a thirtieth aspect of the present disclosure, any of the structure and functionality illustrated and described in connection with FIG. 4 may be used in combination with any one or more of the preceding aspects.

In accordance with a thirty-first aspect of the present disclosure, any of the structure and functionality illustrated and described in connection with FIG. 5 may be used in combination with any one or more of the preceding aspects.

In accordance with a thirty-second aspect of the present disclosure, any of the structure and functionality illustrated and described in connection with FIG. 6 may be used in combination with any one or more of the preceding aspects.

In accordance with a thirty-third aspect of the present disclosure, any of the structure and functionality illustrated and described in connection with FIG. 7 may be used in combination with any one or more of the preceding aspects.

In accordance with a thirty-fourth aspect of the present disclosure, any of the structure and functionality illustrated and described in connection with FIG. 8 may be used in combination with any one or more of the preceding aspects.

In accordance with a thirty-fifth aspect of the present disclosure, any of the structure and functionality illustrated and described in connection with FIG. 9 may be used in combination with any one or more of the preceding aspects.

Figure 10:
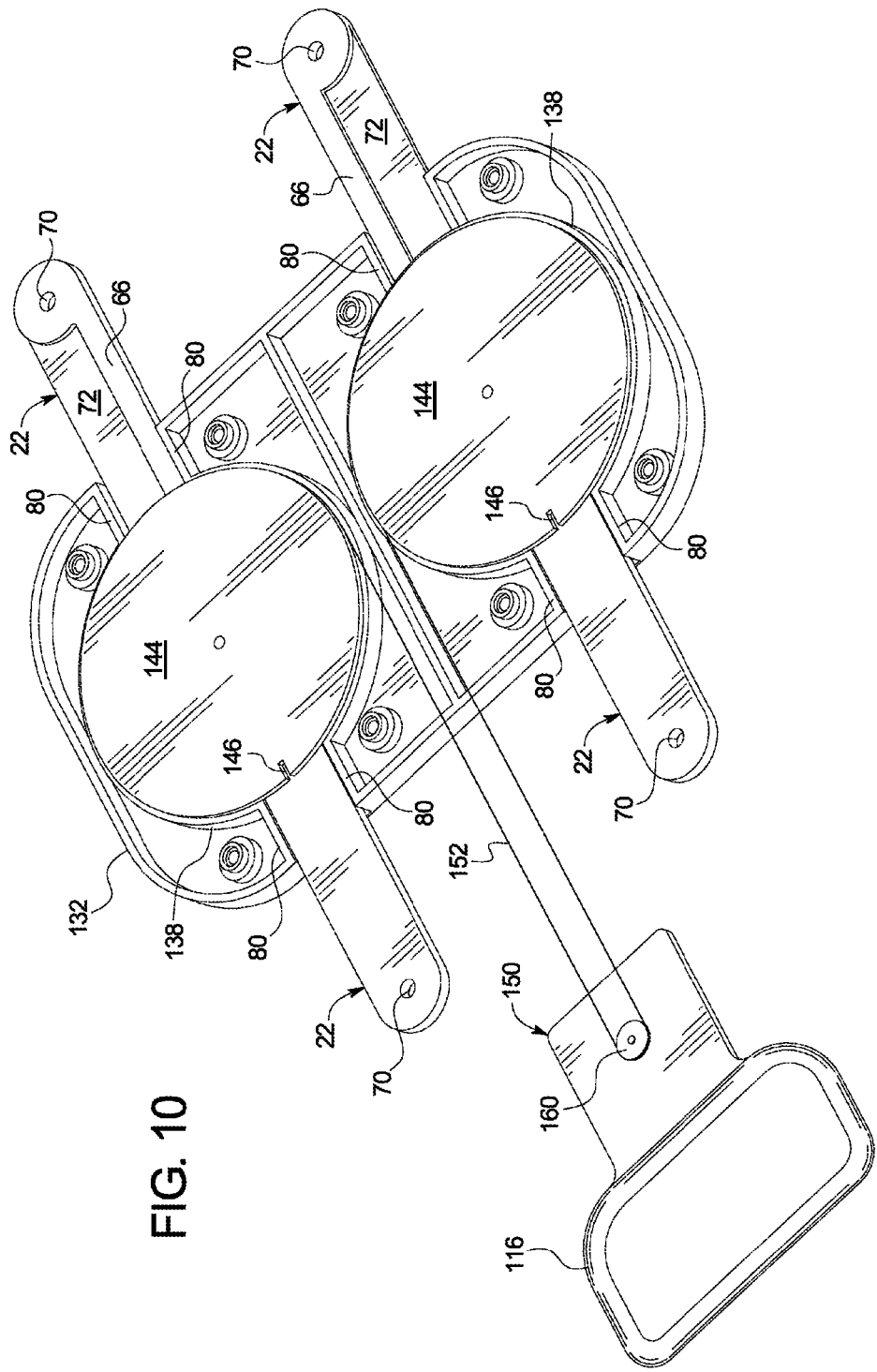
FIG. 10 is the front perspective view of FIG. 8 with the front plate and balancer pulley cover removed to show the large pulleys and balancer pulley, respectively.

In accordance with a thirty-sixth aspect of the present disclosure, any of the structure and functionality illustrated and described in connection with FIG. 10 may be used in combination with any one or more of the preceding aspects.

In accordance with a thirty-seventh aspect of the present disclosure, any of the structure and functionality illustrated and described in connection with FIG. 11 may be used in combination with any one or more of the preceding aspects.

In accordance with a thirty-eighth aspect of the present disclosure, any of the structure and functionality illustrated and described in connection with FIG. 12 may be used in combination with any one or more of the preceding aspects.

In accordance with a thirty-ninth aspect of the present disclosure, any of the structure and functionality illustrated and described in connection with FIG. 13 may be used in combination with any one or more of the preceding aspects.

In accordance with a fortieth aspect of the present disclosure, any of the structure and functionality illustrated and described in connection with FIG. 14 may be used in combination with any one or more of the preceding aspects.

In accordance with a forty-first aspect of the present disclosure, any of the structure and functionality illustrated and described in connection with FIG. 15 may be used in combination with any one or more of the preceding aspects.

In accordance with a forty-second aspect of the present disclosure, any of the structure and functionality illustrated and described in connection with FIG. 16 may be used in combination with any one or more of the preceding aspects.

In accordance with a forty-third aspect of the present disclosure, any of the structure and functionality illustrated and described in connection with FIG. 17 may be used in combination with any one or more of the preceding aspects.

In accordance with a forty-fourth aspect of the present disclosure, any of the structure and functionality illustrated and described in connection with FIG. 18 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An adjustable orthopedic back brace comprising:
a first side panel having a distal end and a proximal end;
a second side panel having a distal end and a proximal end;
a rotating gear in geared communication with a first rack gear, the first rack gear connected to the proximal end of the first side panel, the rotating gear in geared communication with a second rack gear, the second rack gear connected to the proximal end of the second side panel;
a mechanical advantage member rotatable with and providing mechanical advantage for the rotating gear; and
an actuator connected operably to the mechanical advantage member for turning the member and the rotating gear to cause a translational movement of (i) the first rack gear and the first side panel and (ii) the second rack gear and the second side panel.

2. The adjustable orthopedic back brace of claim 1, the rotating gear a first rotating gear, the mechanical advantage member a first mechanical advantage member, and which includes (a) a second rotating gear in geared communication with a third rack gear, the third rack gear connected to the proximal end of the first side panel, the second rotating gear in geared communication with a forth rack gear, the forth rack gear connected to the proximal end of the second side panel; (b) a second mechanical advantage member rotatable with and providing mechanical advantage for the second rotating gear; and (c) the actuator connected operably to the first and second mechanical advantages member to cause a translational movement of (i) the first rack gear, the third rack gear and the first side panel and (ii) the second rack gear, the forth rack gear and the second side panel.

3. The adjustable orthopedic back brace of claim 1, wherein the mechanical advantage member includes a larger rotating gear, the actuator including a rack gear portion operable with the larger rotating gear.

4. The adjustable orthopedic back brace of claim 1, wherein the mechanical advantage member is connected to or integral with the rotating gear.

5. The adjustable orthopedic back brace of claim 1, wherein the mechanical advantage member includes a pulley.

6. The adjustable orthopedic back brace of claim 5, wherein the actuator includes a cord connected to the pulley.

7. The adjustable orthopedic back brace of claim 1, wherein the actuator includes a handle configured to be secured releasably to one of the first and second side panels.

8. The adjustable orthopedic back brace of claim 1, wherein the distal ends of the first and second side panels are configured to be releasably secured together.

9. An adjustable orthopedic back brace comprising:
a first side panel having a distal end and a proximal end;
a second side panel having a distal end and a proximal end;

a first rotating gear in geared communication with a first rack gear, the first rack gear connected to the proximal end of the first side panel, the first rotating gear in geared communication with a second rack gear, the second rack gear connected to the proximal end of the second side panel;

a second rotating gear in geared communication with a third rack gear, the third rack gear connected to the proximal end of the first side panel, the second rotating gear in geared communication with a forth rack gear, the forth rack gear connected to the proximal end of the second side panel;

a first mechanical advantage member rotatable with and providing mechanical advantage for the first rotating gear;

a second mechanical advantage member rotatable with and providing mechanical advantage for the second rotating gear; and an actuator connected operably to the first and second mechanical advantage members for turning the first and second members and the corresponding first and second rotating gears to cause a translational movement of (i) the first rack gear, the third rack gear and the first side panel and (ii) the second rack gear, the forth rack gear and the second side panel.

10. The adjustable orthopedic back brace of claim 9, wherein the first and second mechanical advantage members and the first and second rotating gears are located in a common housing.

11. The adjustable orthopedic back brace of claim 9, wherein at least one of the first and second mechanical advantage members is formed with the corresponding first and second rotating gear.

12. The adjustable orthopedic back brace of claim 9, wherein at lease one of (i) the first and second rack gears and (ii) the third and forth rack gears are mated such that at least a portion of their respective gear teeth lie in a common plane with the respective first or second rotating gear.

13. The adjustable orthopedic back brace of claim 9, wherein the at least one mated set of rack gears has a stepped thickness such that the rack gears mate in an overlapping manner.

14. The adjustable orthopedic back brace of claim 9, wherein at least one of (i) the first and second rack gears and (ii) the third and forth rack gears are mated such that their respective gear teeth lie on opposing sides of the respective first or second rotating gear.

15. The adjustable orthopedic back brace of claim 9, which includes at least one stationary guide for guiding translational movement of at least one of the first, second, third and forth rack gears.

16. The adjustable orthopedic back brace of claim 9, wherein at least one of the first, second, third and forth rack gears defines a slot and has gear teeth formed on a wall defining the slot.

17. The adjustable orthopedic back brace of claim 9, wherein the actuator includes a handle portion for manual movement of the actuator, and wherein the handle portion is configured to releasably attach to one of the first and second side panels to hold the rack gears at a desired position.

18. The adjustable orthopedic back brace of claim 9, wherein one of the first and second side panels includes a channel for receiving and routing a mechanical advantage member actuation portion of the actuator.

19. The adjustable orthopedic back brace of claim 9, wherein at least one of the first and second mechanical advantage members includes a larger rotating gear, the actuator including a rack gear portion operable with the at least one larger rotating gear.

20. The adjustable orthopedic back brace of claim 19, wherein the actuator includes an indented portion adjacent the rack gear portion for holding the actuator in a fully retracted position against the at least one larger rotating gear.

21. The adjustable orthopedic back brace of claim 9, wherein at least one of the first and second mechanical advantage members includes a pulley, and wherein the actuator includes a cord attached to the at least one pulley, the cord running to a handle portion of the actuator.

22. The adjustable orthopedic back brace of claim 21, wherein the handle portion includes a balancer pulley for receiving the cord.

23. An adjustable orthopedic back brace comprising:
a side panel having a distal end and a proximal end;
a first rotating gear in geared communication with a first rack gear, the first rack gear connected to the proximal end of the side panel;
a second rotating gear in geared communication with a second rack gear, the second rack gear connected to the proximal end of the side panel;
a first mechanical advantage member rotatable with and providing mechanical advantage for the first rotating gear;
a second mechanical advantage member rotatable with and providing mechanical advantage for the second rotating gear; and
an actuator connected operably to the first and second mechanical advantage members for turning the members and the corresponding first and second rotating gears to cause a translation movement of the first rack gear, the second rack gear and the side panel.

24. The adjustable orthopedic back brace of claim 23, the side panel a first side panel, and which includes a second side panel having a distal end and a proximal end, the first rotating gear in geared communication additionally with a third rack gear, the third rack gear connected to the proximal end of the second side panel, the second rotating gear in geared communication additionally with a fourth rack gear, the fourth rack gear connected to the proximal end of the second side panel, the actuator connected operably to the first and second mechanical advantage members for turning the members and the corresponding first and second rotating gears to cause a translation movement of (i) the first rack gear, the second rack gear and the first side panel and (ii) the third rack gear, the forth rack gear and the second side panel.

25. The adjustable orthopedic back brace of claim 23, wherein at least one of the first and second mechanical advantage members includes a larger rotating gear, the actuator including a rack gear portion operable with the at least one larger rotating gear.

26. The adjustable orthopedic back brace of claim 23, wherein at least one of the mechanical advantage members includes a pulley.

* * * * *